(12) United States Patent
Jarjour et al.

(10) Patent No.: US 10,000,746 B2
(45) Date of Patent: Jun. 19, 2018

(54) LAGLIDADG HOMING ENDONUCLEASE CLEAVING THE T CELL RECEPTOR ALPHA GENE AND USES THEREOF

(71) Applicants: Cellectics, Paris (FR); Precision Genome Engineering, Inc., Tumwater, WA (US)

(72) Inventors: Jordan Jarjour, Seattle, WA (US); Alexander Astrakhan, Seattle, WA (US)

(73) Assignees: CELLECTIS, Paris (FR); PRECISION GENOME ENGINEERING, INC., Tumwater, WA (US)

( * ) Notice: Subject to any disclaimer, the term of this patent is extended or adjusted under 35 U.S.C. 154(b) by 0 days. days.

(21) Appl. No.: 14/891,216

(22) PCT Filed: May 28, 2014

(86) PCT No.: PCT/EP2014/061189
§ 371 (c)(1),
(2) Date: Nov. 13, 2015

(87) PCT Pub. No.: WO2014/191527
PCT Pub. Date: Dec. 4, 2014

(65) Prior Publication Data
US 2016/0130569 A1  May 12, 2016

(30) Foreign Application Priority Data
May 31, 2013 (DK) .................................. 2013 70303

(51) Int. Cl.
| | | |
|---|---|---|
| *C12N 9/16* | (2006.01) | |
| *C12N 9/22* | (2006.01) | |
| *A61K 38/46* | (2006.01) | |
| *A61K 48/00* | (2006.01) | |

(52) U.S. Cl.
CPC .............. *C12N 9/22* (2013.01); *A61K 38/465* (2013.01); *A61K 48/00* (2013.01)

(58) Field of Classification Search
None
See application file for complete search history.

(56) References Cited

U.S. PATENT DOCUMENTS

2011/0158957 A1 * 6/2011 Bonini .................... C12N 9/22
424/93.7

FOREIGN PATENT DOCUMENTS

WO 2011/156430 A2 12/2011

OTHER PUBLICATIONS

Branden et al. Introduction to Protein Structure, Garland Publishing Inc., New York, p. 247, 1991.*
Baxter. Engineering domain fusion chimeras from I-Onul family LAGLIDADG homing endonucleases for genome engineering applications. University of Washington. 2012.*
Ry0takeuchi et al: " Tapping natural reservoirs o f homing endonucleases for targeted gene modification", Proceedings of the National Academy of Sciences, National Academy of Sciences, vol. 108, No. 32, Aug. 1, 2011 (Aug. 1, 2011), pp. 13077-13082.
Torikai Hiroki et al: "A foundation for universal T-cell based immunotherapy: T cells engineered to express a CD19-specific chimeric-antigen-receptor and eliminate expression of endogenous TCR.", BloodJun. 14, 2012, vol. 119, No. 24, Jun. 14, 2012 (Jun. 14, 2012), pp. 5697-5705.
Baxter Sarah et al: "Engineering domain fusion chimeras from I-Onul family LAGLIDADG homing endonucleases.", Nucleic Acids Research Sep. 2012, vol. 40, No. 16, Sep. 2012 (Sep. 2012), pp. 7985-8000.
Provasi Elena et al: "TCR Gene Editing Results in Effective Immunotherapy of Leukemia without the Development o f GvHD", Blood,American Society of Hematology, US, vol. 118, No. 21, Dec. 13, 2011 (Dec. 13, 2011), p. 307.
Hafez Mohamed et al: "Homing endonucleases: DNA scissors on a mission", Genome, vol. 55, No. 8, Aug. 2012 (Aug. 2012), pp. 553-569.
S. Boissel et al: "megaTALs: a rare-cleaving nuclease architecture for therapeutic genome engineering", Nucleic Acids Research, vol. 42, No. 4, Nov. 26, 2013 (Nov. 26, 2013), pp. 2591-2601.

* cited by examiner

*Primary Examiner* — Yong D Pak
(74) *Attorney, Agent, or Firm* — Arrigo, Lee, Guttmann & Mouta-Bellum LLP

(57) ABSTRACT

Disclosed herein are compositions for inactivating the human TCR-alpha gene comprising engineered LAGLI-DADG homing endonucleases (LHEs) and their derivatives, particularly derived from members of the \-Onul subfamily of LHEs. Polynucleotides encoding such endonucleases, vectors comprising said polynucleotides, cells comprising or having been treated with such endonucleases, and therapeutic compositions deriving therefore are also provided.

21 Claims, 16 Drawing Sheets

TCRA_S02_2E5      MAYMSPRRESINPWILTGFADAEGSTMLDIRNRNSMMYMTSLRFQTFLHNKD
TCRA_2E5_RD2_23   MAYMSRRESINPWILTGFADAEGSFMLDIRNRNSMMYMTSLRFQTFLHNKD

TCRA_S02_2E5      KSILENIQSTWKVGCMTENSGDRAVMLRVTRFEDLKVIIDHFEKYPLITQKLGD
TCRA_2E5_RD2_23   KSILENIQSTWKVGCMTENSMDRAVMLRVTRFEDLKVIIDHFEKYPLITQKLGD

TCRA_S02_2E5      YKLFKQAFSVMENKEHLKENGIKELVRIKAKMNWGLNDELKKAFPENISKERP
TCRA_2E5_RD2_23   YKLFKQAFSVMENKEHLKRNGIKELVRIKAKMNWGLNDELKKAFPENISKERP

TCRA_S02_2E5      LINKNIPNFKWLAGFTSGEGCMIEKNKSEFGWFMVNLEKFSITQHIRDKNLM
TCRA_2E5_RD2_23   LINKNIPNFKWLAGFTMGEGCMIEKNKSEFMWFMVNLEKMSIMHIRDKNLM

TCRA_S02_2E5      NSLITYLGCCIEKNKSEFGWMFVVFKFSDINDKIIPVFQENTLIGVKLED
TCRA_2E5_RD2_23   NSLITYLGCCIMRNKSRFMWLMFVVFKFSDINQKIIPVFQENTLIGVKLED

TCRA_S02_2E5      FEDWCKVAKLIEEKKLTESGLDEIKKIKLNMNKGRVF
TCRA_2E5_RD2_23   FEDWCKVAKLIEEKKLTESGLDEIKKTKLNMNKGRVF

FIG. 5

Untransfected
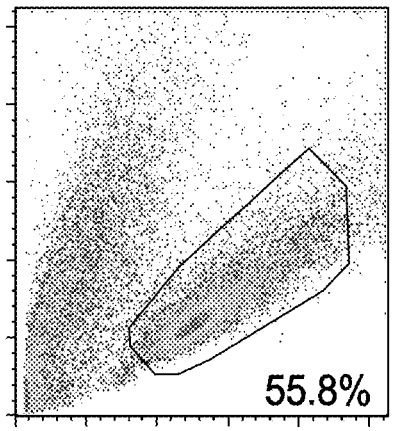
55.8%
BFP
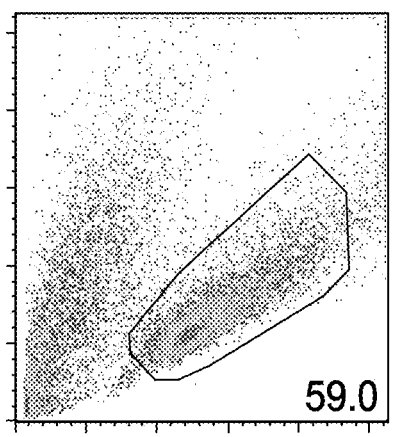
59.0
TCRa-S02-2E5-Refined
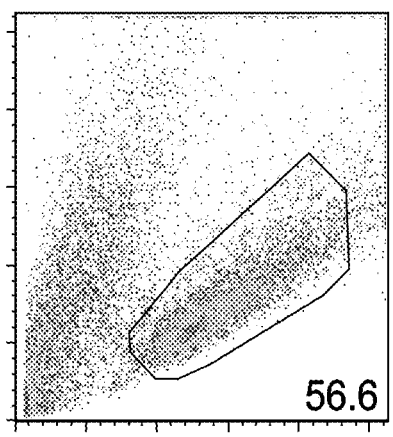
56.6
FIG. 8

| Position | Native | 2E5 | Refined |
|---|---|---|---|
| 24 | Ser | Ser | |
| 26 | Leu | Ile | |
| 28 | Arg | Asp | |
| 30 | Arg | Arg | |
| 32 | Asn | Arg | |
| 34 | Lys | Asn | |
| 35 | Ser | Glu | |
| 36 | Ser | Ser | |
| 37 | Val | Asn | |
| 38 | Gly | Arg | |
| 40 | Ser | Arg | |
| 42 | Glu | Ser | |
| 44 | Gly | Arg | |
| 46 | Gln | Glu | |
| 48 | Thr | Thr | |
| 68 | Val | Lys | |
| 70 | Ala | Thr | |
| 72 | Ser | Ser | |
| 73 | Gly | | Ser |
| 75 | Asn | Arg | |
| 76 | Ala | Ala | |
| 78 | Ser | Met | |
| 80 | Lys | Arg | |
| 82 | Thr | Thr | |
| 176 | Ser | | Ala |
| 180 | Cys | Tyr | |
| 182 | Phe | Gly | |
| 184 | Asn | Asn | |
| 186 | Ile | Lys | |
| 188 | Ser | Val | |
| 189 | Lys | Lys | |
| 190 | Ser | Gly | |
| 191 | Lys | Asn | Thr |
| 192 | Leu | Ala | |
| 193 | Gly | Lys | |
| 195 | Gln | Tyr | |
| 197 | Gln | Gly | |
| 199 | Val | Arg | |
| 201 | Ser | Ser | |
| 203 | Thr | Thr | Ser |
| 223 | Tyr | Ser | |
| 225 | Lys | Arg | Trp |
| 227 | Lys | Lys | |
| 229 | Lys | Lys | |
| 232 | Phe | Phe | |
| 233 | Ser | | Arg |
| 234 | Trp | Trp | |
| 236 | Asp | Glu | |
| 238 | Val | Val | |
| 240 | Thr | Thr | |

FIG. 16

SEQUENCE LISTING

<160> NUMBER OF SEQ ID NOS: 16

<210> SEQ ID NO 1
<211> LENGTH: 909

```
<212> TYPE: DNA
<213> ORGANISM: Ophiostoma novo-ulmi
<220> FEATURE:
<223> OTHER INFORMATION: Wild type I-OnuI

<400> SEQUENCE: 1
atggcataca tgtcgcgcag agagtccatc aacccatgga ttctgactgg tttcgctgat      60
gccgaaggat ccttcttgct gagaatccga acaataaca agagctccgt gggttactct     120
accgagttgg gctttcaaat cactctgcac aacaaggaca atcgattct ggagaatatc     180 cagtcgactt ggaaggtcgg cgtgattgct aactcaggcg acaatgccgt cagtctgaaa     240
gttacgcgtt tcgaagattt gaaagtgatt atcgaccact tcgagaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
ggtctcactg acgaattgaa aaagcatttt ccagagaaca ttagcaaaga gcgccccctt     480
atcaataaga acattccgaa tttcaaatgg ctggctggat tcacatctgg tgaaggctgc     540
ttctttgtga acttgatcaa gtccaaatct aagctgggtg tacaggttca attggtcttc     600
agcattactc agcacatcag agacaagaac ctgatgaatt cattgataac ataccctaggc     660 tgtggttaca tcaaagagaa gaacaagtcc gagttcagtt ggctcgactt tgtggttacc     720
aaattcagcg atatcaacga caagatcatt ccggtattcc aggaaaatac tctgattggc     780
gtcaaactcg aggactttga agattggtgc aaggttgcca aattgatcga agagaagaaa     840
cacctgaccg aatccggttt ggatgagatt aagaaaatca agctgaacat gaacaaaggt     900
cgtgtcttc                                                            909

<210> SEQ ID NO 2
<211> LENGTH: 303
<212> TYPE: PRT
<213> ORGANISM: Ophiostoma novo-ulmi
<220> FEATURE:
<223> OTHER INFORMATION: Wild type I-OnuI

<400> SEQUENCE: 2

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160
```

```
Ile Asn Lys Asn Ile Pro Asn Phe Lys Trp Leu Ala Gly Phe Thr Ser
            165                 170                 175

Gly Glu Gly Cys Phe Phe Val Asn Leu Ile Lys Ser Lys Ser Lys Leu
        180                 185                 190

Gly Val Gln Val Gln Leu Val Phe Ser Ile Thr Gln His Ile Arg Asp
    195                 200                 205

Lys Asn Leu Met Asn Ser Leu Ile Thr Tyr Leu Gly Cys Gly Tyr Ile
210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
            245                 250                 255

Thr Leu Ile Gly Val Lys Leu Glu Asp Phe Glu Asp Trp Cys Lys Val
            260                 265                 270

Ala Lys Leu Ile Glu Glu Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 3
<211> LENGTH: 22
<212> TYPE: DNA
<213> ORGANISM: artificial sequence
<220> FEATURE:
<223> OTHER INFORMATION: Target TCRA_S02

<400> SEQUENCE: 3
tgtctgccta ttcaccgatt tt                                          22

<210> SEQ ID NO 4
<211> LENGTH: 22
<212> TYPE: DNA
<213> ORGANISM: artificial sequence
<220> FEATURE:
<223> OTHER INFORMATION: Target TCRA_S010

<400> SEQUENCE: 4
ctagcacagt tttgtctgtg at                                          22

<210> SEQ ID NO 5
<211> LENGTH: 909
<212> TYPE: DNA
<213> ORGANISM: artificial sequence
<220> FEATURE:
<223> OTHER INFORMATION: LHE CCR5_S02_2E5

<400> SEQUENCE: 5
atggcataca tgtcgcgcag agagtccatc aacccatgga ttctgactgg tttcgctgat      60
gccgaaggat cattcatact agacatccgc aaccgaaaca acgaaagcaa cagataccga     120
acttcgctga gattccagat caccctgcac aacaaggaca atcgattct ggagaatatc      180 cagtcgactt ggaaggtcgg caagatcaca aacagcggcg acagagccgt catgctgagg     240
gtcacccgtt cgaagatttt gaaagtgatt atcgaccact tcgagaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
ggtctcaatg acgaattgaa aaaagcattt ccagagaaca ttagcaaaga gcgccccctt     480
atcaataaga acattccgaa tttcaaatgg ctggctggat tcacatctgg tgaaggctac     540
```

```
ttcggcgtga acctaaaaaa ggtaaagggc aacgcaaagg tatacgtggg actgagattc      600
tcaatcacac agcacatcag agacaagaac ctgatgaatt cattgataac atacctaggc      660
tgtggttcca tcagggagaa gaacaagtct gagttcagtt ggctcgagtt cgtcgtaacc      720
aaattcagcg atatcaacga caagatcatt ccggtattcc aggaaaatac tctgattggc      780
gtcaaactcg aggactttga agattggtgc aaggttgcca aattgatcga agagaagaaa      840
cacctgaccg aatccggttt ggatgagatt aagaaaatca agctgaacat gaacaaaggt      900
cgtgtcttc                                                              909
```

```
<210> SEQ ID NO 6
<211> LENGTH: 303
<212> TYPE: PRT
<213> ORGANISM: artificial sequence
<220> FEATURE:
<223> OTHER INFORMATION: LHE CCR5_S02_2E5

<400> SEQUENCE: 6

Met Ala Tyr Met Ser Arg Arg Glu Ser Ile Asn Pro Trp Ile Leu Thr
1               5                   10                  15

Gly Phe Ala Asp Ala Glu Gly Ser Phe Ile Leu Asp Ile Arg Asn Arg
            20                  25                  30

Asn Asn Glu Ser Asn Arg Tyr Arg Thr Ser Leu Arg Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Thr Asn Ser Gly Asp Arg Ala Val Met Leu Arg
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Glu Gly Tyr Phe Gly Val Asn Leu Lys Lys Val Lys Gly Asn Ala
            180                 185                 190

Lys Val Tyr Val Gly Leu Arg Phe Ser Ile Thr Gln His Ile Arg Asp
        195                 200                 205

Lys Asn Leu Met Asn Ser Leu Ile Thr Tyr Leu Gly Cys Gly Ser Ile
    210                 215                 220

Arg Glu Lys Asn Lys Ser Glu Phe Ser Trp Leu Glu Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
```

<210> SEQ ID NO 7
<211> LENGTH: 909
<212> TYPE: DNA
<213> ORGANISM: artificial sequence
<220> FEATURE:
<223> OTHER INFORMATION: LHE TCRA_S02_2E5_RD1_08

<400> SEQUENCE: 7

```
atggcataca tgtcgcgcag agagtccatc aacccatgga ttctgactgg tttcgctgat      60
gccgaaggat cattcatact agacatccgc aaccgaaaca acgaaagcaa cagataccga     120
acttcgctga gattccagat caccctgcac aacaaggaca atcgattct ggagaatatc     180
cagtcgactt ggaaggtcgg caagatcaca acagcggcg acagagccgt catgctgagg     240
gtcacccgtt tcgaagattt gaaagtgatt atcgaccact tcgagaaata tccgctgatt     300
acccagaaat tgggcgatta caagttgttt aaacaggcat tcagcgtcat ggagaacaaa     360
gaacatctta aggagaatgg gattaaggag ctcgtacgaa tcaaagctaa gatgaattgg     420
ggtctcaacg acgaattgaa aaagcatttt ccagagaaca ttagcaaaga gcgccccctt     480
atcaataaga acattccgaa tttcaaatgg ctggctggat tcacatctgg tgagggctac     540
ttcggcgtga atctaaaaaa ggtaaagggc aacgcaaagg tatacgtggg actgagattc     600
tcaatctcac agcacatcag agacaagaac ctgatgaatt cattgataac atacctaggc     660
tgtggttcca tctgggagaa gaacaagtct gagttcagtt ggctcgagtt cgtcgtaacc     720
aaattcagcg atatcaacga caagatcatt ccggtattcc aggaaaatac tctgattggc     780
gtcaaactcg aggactttga agattggtgc aaggttgcca aattgatcga agagaagaaa     840
cacctgaccg aatccggttt ggatgagatt aagaaaatca agctgaacat gaacaaaggt     900
cgtgtcttc                                                             909
```

<210> SEQ ID NO 8
<211> LENGTH: 303
<212> TYPE: PRT
<213> ORGANISM: artificial sequence
<220> FEATURE:
<223> OTHER INFORMATION: LHE TCRA_S02_2E5_RD1_08

<400> SEQUENCE: 8

```
Met Ala Tyr Met Ser Arg Arg Glu Ser Ile Asn Pro Trp Ile Leu Thr
 1               5                  10                  15

Gly Phe Ala Asp Ala Glu Gly Ser Phe Ile Leu Asp Ile Arg Asn Arg
             20                  25                  30

Asn Asn Glu Ser Asn Arg Tyr Arg Thr Ser Leu Arg Phe Gln Ile Thr
         35                  40                  45

Leu His Asn Lys Asp Lys Ser Ile Leu Glu Asn Ile Gln Ser Thr Trp
     50                  55                  60

Lys Val Gly Lys Ile Thr Asn Ser Gly Asp Arg Ala Val Met Leu Arg
 65                  70                  75                  80

Val Thr Arg Phe Glu Asp Leu Lys Val Ile Ile Asp His Phe Glu Lys
                 85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
```

```
                130               135               140
Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Glu Gly Tyr Phe Gly Val Asn Leu Lys Lys Val Lys Gly Asn Ala
            180                 185                 190

Lys Val Tyr Val Gly Leu Arg Phe Ser Ile Ser Gln His Ile Arg Asp
        195                 200                 205

Lys Asn Leu Met Asn Ser Leu Ile Thr Tyr Leu Gly Cys Gly Ser Ile
    210                 215                 220

Trp Glu Lys Asn Lys Ser Glu Phe Ser Trp Leu Glu Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300
```

<210> SEQ ID NO 9
<211> LENGTH: 909
<212> TYPE: DNA
<213> ORGANISM: artificial sequence
<220> FEATURE:
<223> OTHER INFORMATION: LHE TCRA_S02_2E5_RD2_23

<400> SEQUENCE: 9

```
atggcataca tgtcgcgcag agagtccatc aacccatgga ttctgactgg tttcgctgat      60
gccgaaggat cattcatact agacatccgc aaccgaaaca cgaaagcaa cagataccga     120
acttcgctga gattccagat caccctgcac aacaaggaca atcgattct ggagaatatc     180
cagtcgactt ggaaggtcgg caagatcaca aacagcagtg acagagccgt catgctgagg     240
gtcacccgtt tcgaagattt gaaagtgatt atcgaccact tcgagaaata tccgctgatt     300
acccagaaat tgggcgatta caagttgttt aaacaggcat tcagcgtcat ggagaataaa     360
gaacatctta aggagaatgg gattaaggag ctcgtacgaa tcaaagctaa gatgaattgg     420
ggtctcaatg acgaattgaa aaaagcattt ccagagaaca ttagcaaaga gcgccccctt     480
atcaataaga acattccgaa tttcaaatgg ctggctggat tcacagctgg tgaaggctac     540
ttcggcgtga tctaaaaaaa ggtaaagggc accgcaaagg tatacgtggg actgagattc     600
tcaatctcac agcacatcag agacaagaac ctgatgaatt cattgataac atacctaggc     660
tgtggttcca tctgggagaa gaacaagtct gagttcagat ggctcgagtt cgtcgtaacc     720
aaattcagcg atatcaacga caagatcatt ccggtattcc aggaaaatac tctgattggc     780
gtcaaactcg aggactttga agattggtgc aaggttgcca aattgatcga agagaagaaa     840
cacctgaccg aatccggttt ggatgagatt aagaaaatca gctgaacat gaacaaaggt     900
cgtgtcttc                                                             909
```

<210> SEQ ID NO 10
<211> LENGTH: 303
<212> TYPE: PRT
<213> ORGANISM: artificial sequence

<220> FEATURE:
<223> OTHER INFORMATION: LHE TCRA_S02_2E5_RD2_23

<400> SEQUENCE: 10

Met Ala Tyr Met Ser Arg Arg Glu Ser Ile Asn Pro Trp Ile Leu Thr
1               5                   10                  15

Gly Phe Ala Asp Ala Glu Gly Ser Phe Ile Leu Asp Ile Arg Asn Arg
            20                  25                  30

Asn Asn Glu Ser Asn Arg Tyr Arg Thr Ser Leu Arg Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Thr Asn Ser Ser Asp Arg Ala Val Met Leu Arg
65              70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Gly Arg Pro Leu
145                 150                 155                 160

Ile Asn Lys Asn Ile Pro Asn Phe Lys Trp Leu Ala Gly Phe Thr Ala
                165                 170                 175

Gly Glu Gly Tyr Phe Gly Val Asn Leu Lys Lys Val Lys Gly Thr Ala
            180                 185                 190

Lys Val Tyr Val Gly Leu Arg Phe Ser Ile Ser Gln His Ile Arg Asp
    195                 200                 205

Lys Asn Leu Met Asn Ser Leu Ile Thr Tyr Leu Gly Cys Gly Ser Ile
    210                 215                 220

Trp Glu Lys Asn Lys Ser Glu Phe Arg Trp Leu Glu Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
    275                 280                 285

Glu Ile Lys Lys Ile Lys Leu Asn Met Asn Lys Gly Arg Val Phe
    290                 295                 300

<210> SEQ ID NO 11
<211> LENGTH: 22
<212> TYPE: DNA
<213> ORGANISM: artificial sequence
<220> FEATURE:
<223> OTHER INFORMATION: Target Onu-I wild type

<400> SEQUENCE: 11
tttccactta ttcaaccttt ta                                          22

<210> SEQ ID NO 12
<211> LENGTH: 7842
<212> TYPE: DNA
<213> ORGANISM: artificial sequence
<220> FEATURE:
<223> OTHER INFORMATION: TCRA_S02 LHE lentiviral vector

<400> SEQUENCE: 12

| | | |
|---|---|---|
| gacgtcaatg tagtcttatg caatactctt gtagtcttgc aacatggtaa cgatgagtta | 60 |
| gcaacatgcc ttacaaggag agaaaaagca ccgtgcatgc cgattggtgg aagtaaggtg | 120 |
| gtacgatcgt gccttattag gaaggcaaca cagggtctg acatggattg gacgaaccac | 180 |
| tgaattgccg cattgcagag atattgtatt taagtgccta gctcgataca taaacgggtc | 240 |
| tctctggtta gaccagatct gagcctggga gctctctggc taactaggga acccactgct | 300 |
| taagcctcaa taagcttgc cttgagtgct tcaagtagtg tgtgcccgtc tgttgtgtga | 360 |
| ctctggtaac tagagatccc tcagacccttt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta aaggagaga atgggtgcg agagcgtcag tattaagcgg | 600 |
| gggagaatta gatcgcgatg ggaaaaaatt cggttaaggc cagggggaaa gaaaaaatat | 660 |
| aaattaaaac atatagtatg gcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga gagcaaaac | 900 |
| aaaagtaaga ccaccgcaca gcaagcggcc ctgatcttca gacctggagg aggagatatg | 960 |
| agggacaatt ggagaagtga attatataaa tataaagtag taaaaattga accattagga | 1020 |
| gtagcaccca ccaaggcaaa gagaagagtg gtgcagagag aaaaaagagc agtgggaata | 1080 |
| ggagctttgt tccttgggtt cttgggagca gcaggaagca ctatgggcgc agcgtcaatg | 1140 |
| acgctgacgg tacaggccag acaattattg tctggtatag tgcagcagca gaacaatttg | 1200 |
| ctgagggcta ttgaggcgca acagcatctg ttgcaactca cagtctgggg catcaagcag | 1260 |
| ctccaggcaa gaatcctggc tgtggaaaga tacctaaagg atcaacagct cctgggggatt | 1320 |
| tggggttgct ctggaaaact catttgcacc actgctgtgc cttggaatgc tagttggagt | 1380 |
| aatgaatctc tggaacagat ttggaatcac acgacctgga tggagtggga cagagaaatt | 1440 |
| aacaattaca caagcttaat acactcctta attgaagaat cgcaaaacca gcaagaaaag | 1500 |
| aatgaacaag aattattgga attagataaa tgggcaagtt tgtggaattg gtttaacata | 1560 |
| acaaattggc tgtggtatat aaaattattc ataatgatag taggaggctt ggtaggttta | 1620 |
| agaatagttt ttgctgtact ttctatagtg aatagagtta ggcagggata ttcaccatta | 1680 |
| tcgtttcaga cccacctccc aaccccgagg ggacccgaca ggcccgaagg aatagaagaa | 1740 |
| gaaggtggag agagagacag agacagatcc attcgattag tgaacggatc tcgacggtat | 1800 |
| cggttaacttt taaaagaaa agggggggatt ggggggtaca gtgcagggga agaatagta | 1860 |
| gacataatag caacagacat acaaactaaa gaattacaaa aacaaattac aaaaattcaa | 1920 |
| aattttatcg attacgcgtc acgtgctagc tgcagtaacg ccattttgca aggcatggaa | 1980 |
| aaataccaaa ccaagaatag agaagttcag atcaagggcg ggtacatgaa aatagctaac | 2040 |
| gttgggccaa acaggatatc tgcggtgagc agtttcggcc ccggcccggg gccaagaaca | 2100 |
| gatggtcacc gcagtttcgg ccccggcccg aggccaagaa cagatggtcc ccagatatgg | 2160 |
| cccaacccct agcagtttct taagacccat cagatgtttc caggctcccc caaggacctg | 2220 |

-continued

```
aaatgaccct gcgccttatt tgaattaacc aatcagcctg cttctcgctt ctgttcgcgc    2280
gcttctgctt cccgagctct ataaaagagc tcacaacccc tcactcggcg cgccagtcct    2340
ccgacagact gagtcgcccg ctcgagccgc caccatggga tatccatacg atgtcccaga    2400
ttatgcgcca cctaagaaga aacgcaaagt cacgcgatcg cgcagagagt ccatcaaccc    2460
atggattctg actggtttcg ctgatgccga aggatcattc atactagaca tccgcaaccg    2520
aaacaacgaa agcaacagat accgaacttc gctgagattc cagatcaccc tgcacaacaa    2580
ggacaaatcg attctggaga atatccagtc gacttggaag gtcggcaaga tcacaaacag    2640
cagtgacaga gccgtcatgc tgagggtcac ccgtttcgaa gatttgaaag tgattatcga    2700
ccacttcgag aaatatccgc tgattaccca gaaattgggc gattacaagt tgtttaaaca    2760
ggcattcagc gtcatggaga ataaagaaca tcttaaggag aatgggatta aggagctcgt    2820
acgaatcaaa gctaagatga attggggtct caatgacgaa ttgaaaaaag catttccaga    2880
gaacattagc aaagagcgcc cccttatcaa taagaacatt ccgaatttca aatggctggc    2940
tggattcaca gctggtgaag gctacttcgg cgtgaatcta aaaaaggtaa agggcaccgc    3000
aaaggtatac gtgggactga gattctcaat ctcacagcac atcagagaca agaacctgat    3060
gaattcattg ataacatacc taggctgtgg ttccatctgg gagaagaaca agtctgagtt    3120
cagatggctc gagttcgtcg taaccaaatt cagcgatatc aacgacaaga tcattccggt    3180
attccaggaa aatactctga ttggcgtcaa actcgaggac tttgaagatt ggtgcaaggt    3240
tgccaaattg atcgaagaga agaaacacct gaccgaatcc ggtttggatg agattaagaa    3300
aatcaagctg aacatgaaca aaggtcgtgt cttcagcggc cgctcctgat agtaatgacc    3360
tgcaggtcga gcatgcatct agggcggcca attccgcccc tctcccccc cccctctcc    3420 ctccccccc cctaacgtta ctggccgaag ccgcttggaa taaggccggt gtgcgtttgt    3480
ctatatgtta ttttccacca tattgccgtc ttttggcaat gtgagggccc ggaaacctgg    3540
ccctgtcttc ttgacgagca ttcctagggg tctttcccct ctcgccaaag gaatgcaagg    3600
tctgttgaat gtcgtgaagg aagcagttcc tctggaagct tcttgaagac aaacaacgtc    3660
tgtagcgacc ctttgcaggc agcggaaccc cccacctggc gacaggtgcc tctgcggcca    3720
aaagccacgt gtataagata cacctgcaaa ggcggcacaa ccccagtgcc acgttgtgag    3780
ttggatagtt gtggaaagag tcaaatggct ctcctcaagc gtattcaaca aggggctgaa    3840
ggatgcccag aaggtacccc attgtatggg atctgatctg gggcctcggt gcacatgctt    3900
tacatgtgtt tagtcgaggt taaaaaaacg tctaggcccc ccgaaccacg ggacgtggt    3960 tttcctttga aaaacacgat gataagcttg ccacaaccct taccggtcgc caccatgagc    4020
gagctgatta aggagaacat gcacatgaag ctgtacatgg agggcaccgt ggacaaccat    4080
cacttcaagt gcacatccga gggcgaaggc aagccctacg agggcaccca gaccatgaga    4140
atcaaggtgg tcgagggcgg ccctctcccc ttcgccttcg acatcctggc tactagcttc    4200
ctctacggca gcaagacctt catcaaccac acccagggca tccccgactt cttcaagcag    4260
tccttccctg agggcttcac atgggagaga gtcaccacat acgaagacgg gggcgtgctg    4320
accgctaccc aggacaccag cctccaggac ggctgcctca tctacaacgt caagatcaga    4380
ggggtgaact tcacatccaa cggccctgtg atgcagaaga aaacactcgg ctgggaggcc    4440
ttcaccgaga cgctgtaccc cgctgacggc ggcctggaag cagaaacga catggccctg    4500 aagctcgtgg gcgggagcca tctgatcgca aacatcaaga ccacatatag atccaagaaa    4560
cccgctaaga acctcaagat gcctggcgtc tactatgtgg actacagact ggaaagaatc    4620
```

```
aaggaggcca acaacgagac ctacgtcgag cagcacgagg tggcagtggc cagatactgc    4680
gacctcccta gcaaactggg gcacaagctt aattgattct agagtcgacc gagcatctta    4740
ccgccattta tacccatatt tgttctgttt ttcttgattt gggtatacat ttaaatgtta    4800
atagaacaaa atggtggggc aatcatttac atttttaggg atatgtaatt actagttcag    4860
gtgtattgcc acaagacaaa catgttaaga aactttcccg ttatttacgc tctgttcctg    4920
ttaatcaacc tctggattac aaaatttgtg aaagattgac tgatattctt aactatgttg    4980
ctccttttac gctgtgtgga tatgctgctt tatagcctct gtatctagct attgcttccc    5040
gtacggcttt cgttttctcc tccttgtata aatcctggtt gctgtctctt ttagaggagt    5100
tgtggcccgt tgtccgtcaa cgtggcgtgg tgtgctctgt gtttgctgac gcaaccccca    5160
ctggctgggg cattgccacc acctgtcaac tcctttctgg gactttcgct ttccccctcc    5220
cgatcgccac ggcagaactc atcgccgcct gccttgcccg ctgctggaca ggggctaggt    5280
tgctgggcac tgataattcc gtggtgttgt catcggtacc ttttttaaaag aaaagggggg    5340 actggaaggg ctaattcact cccaacgaag acaagatatc ataacttcgt atagcataca    5400
ttatacgaag ttataattta tttgtgaaat ttgtgatgct attgctttat ttgtaaccat    5460
atgtttattt gtgaaatttg tgatgctatt gctttatttg taaccattgc tttttgcttg    5520
tactgggtct ctctggttag accagatctg agcctgggag ctctctggct aactagggaa    5580
cccactgctt aagcctcaat aaagcttgcc tcgaccagcc tcgactgtgc cttctagttg    5640
ccagccatct gttgtttgcc cctcccccgt gccttccttg acctggaag gtgccactcc    5700 cactgtcctt tcctaataaa atgaggaaat tgcatcgcat tgtctgagta ggtgtcattc    5760
tattctgggg ggtggggtgg ggcaggacag caaggggag gattgggaag acaatagcag    5820
gcatgctggg gatgcggtgg gctctatggc ctgcagctgc attaatgaat cggccaacgc    5880
gcggggagag gcggtttgcg tattgggcgc tcttccgctt cctcgctcac tgactcgctg    5940
cgctcggtcg ttcggctgcg gcgagcggta tcagctcact caaaggcggt aatacggtta    6000
tccacagaat caggggataa cgcaggaaag aacatgtgag caaaaggcca gcaaaaggcc    6060
aggaaccgta aaaaggccgc gttgctggcg ttttttccata ggctccgccc ccctgacgag    6120
catcacaaaa atcgacgctc aagtcagagg tggcgaaacc cgacaggact ataaagatac    6180
caggcgtttc cccctggaag ctccctcgtg cgctctcctg ttccgaccct gccgcttacc    6240
ggatacctgt ccgcctttct cccttcggga agcgtggcgc tttctcatag ctcacgctgt    6300
aggtatctca gttcggtgta ggtcgttcgc tccaagctgg gctgtgtgca cgaacccccc    6360
gttcagcccg accgctgcgc cttatccggt aactatcgtc ttgagtccaa cccggtaaga    6420
cacgacttat cgccactggc agcagccact ggtaacagga ttagcagagc gaggtatgta    6480
ggcggtgcta cagagttctt gaagtggtgg cctaactacg gctacactag aaggacagta    6540
tttggtatct gcgctctgct gaagccagtt accttcggaa aaagagttgg tagctcttga    6600
tccggcaaac aaaccaccgc tggtagcggt ggtttttttg tttgcaagca gcagattacg    6660
cgcagaaaaa aaggatctca agaagatcct ttgatctttt ctacggggtc tgacgctcag    6720
tggaacgaaa actcacgtta agggattttg gtcatgagat tatcaaaaag gatcttcacc    6780
tagatccttt taaattaaaa atgaagtttt aaatcaatct aaagtatata tgagtaaact    6840
tggtctgaca gttaccaatg cttaatcagt gaggcaccta tctcagcgat ctgtctattt    6900
cgttcatcca tagttgcctg actccccgtc gtgtagataa ctacgatacg ggagggctta    6960
```

-continued

```
ccatctggcc ccagtgctgc aatgataccg cgagacccac gctcaccggc tccagattta      7020
tcagcaataa accagccagc cggaagggcc gagcgcagaa gtggtcctgc aactttatcc      7080
gcctccatcc agtctattaa ttgttgccgg gaagctagag taagtagttc gccagttaat      7140
agtttgcgca acgttgttgc cattgctaca ggcatcgtgg tgtcacgctc gtcgtttggt      7200
atggcttcat tcagctccgg ttcccaacga tcaaggcgag ttacatgatc ccccatgttg      7260
tgcaaaaaag cggttagctc cttcggtcct ccgatcgttg tcagaagtaa gttggccgca      7320
gtgttatcac tcatggttat ggcagcactg cataattctc ttactgtcat gccatccgta      7380
agatgctttt ctgtgactgg tgagtactca accaagtcat tctgagaata gtgtatgcgg      7440
cgaccgagtt gctcttgccc ggcgtcaata cgggataata ccgcgccaca tagcagaact      7500
ttaaaagtgc tcatcattgg aaaacgttct cggggcgaaa actctcaag gatcttaccg       7560 ctgttgagat ccagttcgat gtaacccact cgtgcaccca actgatcttc agcatctttt      7620
actttcacca gcgtttctgg gtgagcaaaa acaggaaggc aaaatgccgc aaaaaaggga      7680
ataagggcga cacggaaatg ttgaatactc atactcttcc ttttcaata ttattgaagc       7740 atttatcagg gttattgtct catgagcgga tacatatttg aatgtattta gaaaaataaa      7800 caaataggg ttccgcgcac atttccccga aaagtgccac ct                          7842
```

<210> SEQ ID NO 13
<211> LENGTH: 2661
<212> TYPE: DNA
<213> ORGANISM: artificial sequence
<220> FEATURE:
<223> OTHER INFORMATION: MegaTal TCRA_S02

<400> SEQUENCE: 13

```
atgggatcct gcaggtatcc atatgatgtc ccagattatg cgccacctaa gaagaaacgc       60
aaagtcgtgg atctacgcac gctcggctac agtcagcagc agcaagagaa gatcaaaccg      120
aaggtgcgtt cgacagtggc gcagcaccac gaggcactgg tgggccatgg gtttacacac      180
gcgcacatcg ttgcgctcag ccaacacccg gcagcgttag ggaccgtcgc tgtcacgtat      240
cagcacataa tcacggcgtt gccagaggcg acacacgaag acatcgttgg cgtcggcaaa      300
cagtggtccg gcgcacgcgc cctggaggcc ttgctcacgg atgcggggga gttgagaggt      360
ccgccgttac agttggacac aggccaactt gtgaagattg caaaacgtgg cggcgtgacc      420
gcaatggagg cagtgcatgc atcgcgcaat gcactgacgg gtgcccccct gaacctgacc      480
ccggaccaag tggtggctat cgccagcaac attggcggca agcaagcgct cgaaacggtg      540
cagcggctgt tgccggtgct gtgccaggac catggcctga ccccggacca agtggtggct      600
atcgccagca acattggcgg caagcaagcg ctcgaaacgg tgcagcggct gttgccggtg      660
ctgtgccagg accatggcct gaccccggac caagtggtgg ctatcgccag caacattggc      720
ggcaagcaag cgctcgaaac ggtgcagcgg ctgttgccgg tgctgtgcca ggaccatggc      780
ctgaccccgg accaagtggt ggctatcgcc agcaacggtg gcggcaagca agcgctcgaa      840
acggtgcagc ggctgttgcc ggtgctgtgc caggaccatg gcctgactcc ggaccaagtg      900
gtggctatcg ccagccacga tgcggcaag caagcgctcg aaacggtgca gcggctgttg       960
ccggtgctgt gccaggacca tggcctgact ccggaccaag tggtggctat cgccagccac     1020
gatggcggca gcaagcgct cgaaacggtg cagcggctgt tgccggtgct gtgccaggac      1080
catggcctga ccccggacca agtggtggct atcgccagca acattggcgg caagcaagcg     1140
ctcgaaacgg tgcagcggct gttgccggtg ctgtgccagg accatggcct gaccccggac     1200
```

-continued

```
caagtggtgg ctatcgccag caacaatggc ggcaagcaag cgctcgaaac ggtgcagcgg    1260
ctgttgccgg tgctgtgcca ggaccatggc ctgaccccgg accaagtggt ggctatcgcc    1320
agcaacggtg cggcaagca agcgctcgaa acggtgcagc ggctgttgcc ggtgctgtgc     1380
caggaccatg gcctgacccc ggaccaagtg gtggctatcg ccagcaacaa tggcggcaag    1440
caagcgctcg aaacggtgca gcggctgttg ccggtgctgt gccaggacca tggcctgacc    1500
ccggaccaag tggtggctat cgccagcaac attggcggca agcaagcgct cgaaagcatt    1560
gtggcccagc tgagccggcc tgatccggcg ttggccgcgt tgaccaacga ccacctcgtc    1620
gccttggcct gctcggcgg acgtcctgcc atggatgcag tgaaaaaggg attgccgcac     1680
gcgccggaat tgatcagaag agtcaatcgc cgtattggcg aacgcacgtc ccatcgcgtt    1740
gcgatatcta gagtgggagg aagctctcgc agagagtcca tcaacccatg gattctgact    1800
ggtttcgctg atgccgaagg atcattcata ctagacatcc gcaaccgaaa caacgaaagc    1860
aacagatacc gaacttcgct gagattccag atcaccctgc acaacaagga caaatcgatt    1920
ctggagaata tccagtcgac ttggaaggtc ggcaagatca caaacagcag tgacagagcc    1980
gtcatgctga gggtcacccg tttcgaagat ttgaaagtga ttatcgacca cttcgagaaa    2040
tatccgctga ttacccagaa attgggcgat tacaagttgt ttaaacaggc attcagcgtc    2100
atggagaata agaacatct taaggagaat gggattaagg agctcgtacg aatcaaagct     2160
aagatgaatt ggggtctcaa tgacgaattg aaaaaagcat tccagagaa cattagcaaa     2220 gagcgcccc ttatcaataa gaacattccg aatttcaaat ggctggctgg attcacagct    2280
ggtgaaggct acttcggcgt gaatctaaaa aaggtaaagg gcaccgcaaa ggtatacgtg    2340
ggactgagat tctcaatctc acagcacatc agagacaaga acctgatgaa ttcattgata    2400
acatacctag gctgtggttc catctgggag aagaacaagt ctgagttcag atggctcgag    2460
ttcgtcgtaa ccaaattcag cgatatcaac gacaagatca ttccggtatt ccaggaaaat    2520
actctgattg gcgtcaaact cgaggacttt gaagattggt gcaaggttgc caaattgatc    2580
gaagagaaga acacctgac cgaatccggt ttggatgaga ttaagaaaat caagctgaac    2640
atgaacaaag gtcgtgtctt c                                              2661
```

<210> SEQ ID NO 14
<211> LENGTH: 886
<212> TYPE: PRT
<213> ORGANISM: artificial sequence
<220> FEATURE:
<223> OTHER INFORMATION: MegaTal TCRA_S02

<400> SEQUENCE: 14

```
Met Gly Ser Cys Arg Tyr Pro Tyr Asp Val Pro Asp Tyr Ala Pro Pro
1               5                   10                  15

Lys Lys Lys Arg Lys Val Val Asp Leu Arg Thr Leu Gly Tyr Ser Gln
                20                  25                  30

Gln Gln Gln Glu Lys Ile Lys Pro Lys Val Arg Ser Thr Val Ala Gln
            35                  40                  45

His His Glu Ala Leu Val Gly His Gly Phe Thr His Ala His Ile Val
        50                  55                  60

Ala Leu Ser Gln His Pro Ala Ala Leu Gly Thr Val Ala Val Thr Tyr
65                  70                  75                  80

Gln His Ile Ile Thr Ala Leu Pro Glu Ala Thr His Glu Asp Ile Val
                85                  90                  95
```

-continued

Gly Val Gly Lys Gln Trp Ser Gly Ala Arg Ala Leu Glu Ala Leu Leu
               100                 105                 110
Thr Asp Ala Gly Glu Leu Arg Gly Pro Pro Leu Gln Leu Asp Thr Gly
           115                 120                 125
Gln Leu Val Lys Ile Ala Lys Arg Gly Gly Val Thr Ala Met Glu Ala
       130                 135                 140
Val His Ala Ser Arg Asn Ala Leu Thr Gly Ala Pro Leu Asn Leu Thr
145                 150                 155                 160
Pro Asp Gln Val Val Ala Ile Ala Ser Asn Ile Gly Gly Lys Gln Ala
                   165                 170                 175
Leu Glu Thr Val Gln Arg Leu Leu Val Leu Cys Gln Asp His Gly Leu
               180                 185                 190
Thr Pro Asp Gln Val Val Ala Ile Ala Ser Asn Ile Gly Gly Lys Gln
           195                 200                 205
Ala Leu Glu Thr Val Gln Arg Leu Leu Pro Val Leu Cys Gln Asp His
       210                 215                 220
Gly Leu Thr Pro Asp Gln Val Val Ala Ile Ala Ser Asn Ile Gly Gly
225                 230                 235                 240
Lys Gln Ala Leu Glu Thr Val Gln Arg Leu Leu Pro Val Leu Cys Gln
                   245                 250                 255
Asp His Gly Leu Thr Pro Asp Gln Val Val Ala Ile Ala Ser Asn Gly
               260                 265                 270
Gly Gly Lys Gln Ala Leu Glu Thr Val Gln Arg Leu Leu Pro Val Leu
           275                 280                 285
Cys Gln Asp His Gly Leu Thr Pro Asp Gln Val Val Ala Ile Ala Ser
       290                 295                 300
His Asp Gly Gly Lys Gln Ala Leu Glu Thr Val Gln Arg Leu Leu Pro
305                 310                 315                 320
Val Leu Cys Gln Asp His Gly Leu Thr Pro Asp Gln Val Val Ala Ile
                   325                 330                 335
Ala Ser His Asp Gly Gly Lys Gln Ala Leu Glu Thr Val Gln Arg Leu
               340                 345                 350
Leu Pro Val Leu Cys Gln Asp His Gly Leu Thr Pro Asp Gln Val Val
           355                 360                 365
Ala Ile Ala Ser Asn Ile Gly Gly Lys Gln Ala Leu Glu Thr Val Gln
       370                 375                 380
Arg Leu Leu Pro Val Leu Cys Gln Asp His Gly Leu Thr Pro Asp Gln
385                 390                 395                 400
Val Val Ala Ile Ala Ser Asn Asn Gly Gly Lys Gln Ala Leu Glu Thr
                   405                 410                 415
Val Gln Arg Leu Leu Pro Val Leu Cys Gln Asp His Gly Leu Thr Pro
               420                 425                 430
Asp Gln Val Val Ala Ile Ala Ser Asn Gly Gly Gly Lys Gln Ala Leu
           435                 440                 445
Glu Thr Val Gln Arg Leu Leu Pro Val Leu Cys Gln Asp His Gly Leu
       450                 455                 460
Thr Pro Asp Gln Val Val Ala Ile Ala Ser Asn Asn Gly Gly Lys Gln
465                 470                 475                 480
Ala Leu Glu Thr Val Gln Arg Leu Leu Pro Val Leu Cys Gln Asp His
                   485                 490                 495
Gly Leu Thr Pro Asp Gln Val Val Ala Ile Ala Ser Asn Ile Gly Gly
               500                 505                 510
Lys Gln Ala Leu Glu Ser Ile Val Ala Gln Leu Ser Arg Pro Asp Pro

```
            515                 520                 525
Ala Leu Ala Leu Thr Asn Asp His Leu Val Ala Leu Ala Cys Leu
530                 535                 540

Gly Gly Arg Pro Ala Met Asp Ala Val Lys Lys Gly Leu Pro His Ala
545                 550                 555                 560

Pro Glu Leu Ile Arg Arg Val Asn Arg Arg Ile Gly Glu Arg Thr Ser
                565                 570                 575

His Arg Val Ala Ile Ser Arg Val Gly Gly Ser Ser Arg Arg Glu Ser
                580                 585                 590

Ile Asn Pro Trp Ile Leu Thr Gly Phe Ala Asp Ala Glu Gly Ser Phe
            595                 600                 605

Ile Leu Asp Ile Arg Asn Arg Asn Asn Glu Ser Asn Arg Tyr Arg Thr
610                 615                 620

Ser Leu Arg Phe Gln Ile Thr Leu His Asn Lys Asp Lys Ser Ile Leu
625                 630                 635                 640

Glu Asn Ile Gln Ser Thr Trp Lys Val Gly Lys Ile Thr Asn Ser Gly
                645                 650                 655

Asp Arg Ala Val Met Leu Arg Val Thr Arg Phe Glu Asp Leu Lys Val
                660                 665                 670

Ile Ile Asp His Phe Glu Lys Tyr Pro Leu Ile Thr Gln Lys Leu Gly
            675                 680                 685

Asp Tyr Lys Leu Phe Lys Gln Ala Phe Ser Val Met Glu Asn Lys Glu
690                 695                 700

His Leu Lys Glu Asn Gly Ile Lys Glu Leu Val Arg Ile Lys Ala Lys
705                 710                 715                 720

Met Asn Trp Gly Leu Thr Asp Glu Leu Lys Lys Ala Phe Pro Glu Asn
                725                 730                 735

Ile Ser Lys Glu Arg Pro Leu Ile Asn Lys Asn Ile Pro Asn Phe Lys
            740                 745                 750

Trp Leu Ala Gly Phe Thr Ser Gly Asp Gly Tyr Phe Gly Val Asn Leu
            755                 760                 765

Lys Lys Val Lys Gly Asn Ala Lys Val Tyr Val Gly Leu Arg Phe Ser
770                 775                 780

Ile Ser Gln His Ile Arg Asp Lys Asn Leu Met Asn Ser Leu Ile Thr
785                 790                 795                 800

Tyr Leu Gly Cys Gly Ser Ile Trp Glu Lys Asn Lys Ser Glu Phe Ser
                805                 810                 815

Trp Leu Glu Phe Val Val Thr Lys Phe Ser Asp Ile Asn Asp Lys Ile
            820                 825                 830

Ile Pro Val Phe Gln Glu Asn Thr Leu Ile Gly Val Lys Leu Glu Asp
            835                 840                 845

Phe Glu Asp Trp Cys Lys Val Ala Lys Leu Ile Glu Glu Lys Lys His
850                 855                 860

Leu Thr Glu Ser Gly Leu Asp Glu Ile Lys Lys Ile Lys Leu Asn Met
865                 870                 875                 880

Asn Lys Gly Arg Val Phe

<210> SEQ ID NO 15
<211> LENGTH: 3378
<212> TYPE: DNA
<213> ORGANISM: artificial sequence
<220> FEATURE:
<223> OTHER INFORMATION: MegaTal TCRA_S02_Trex2

<400> SEQUENCE: 15
```

```
atgggatcct gcaggtatcc atatgatgtc ccagattatg cgccacctaa gaagaaacgc      60
aaagtcgtgg atctacgcac gctcggctac agtcagcagc agcaagagaa gatcaaaccg     120
aaggtgcgtt cgacagtggc gcagcaccac gaggcactgg tgggccatgg gtttacacac     180
gcgcacatcg ttgcgctcag ccaacacccg gcagcgttag gaccgtcgc tgtcacgtat      240 cagcacataa tcacggcgtt gccagaggcg acacacgaag acatcgttgg cgtcggcaaa     300
cagtggtccg cgcacgcgc cctggaggcc ttgctcacgg atgcgggga gttgagaggt       360 ccgccgttac agttggacac aggccaactt gtgaagattg caaaacgtgg cggcgtgacc     420
gcaatggagg cagtgcatgc atcgcgcaat gcactgacgg gtgcccccct gaacctgacc     480
ccggaccaag tggtggctat cgccagcaac attggcggca agcaagcgct cgaaacggtg     540
cagcggctgt tgccggtgct gtgccaggac catggcctga ccccggacca agtggtggct     600
atcgccagca acattggcgg caagcaagcg ctcgaaacgg tgcagcggct gttgccggtg     660
ctgtgccagg accatggcct gaccccggac caagtggtgg ctatcgccag caacattggc     720
ggcaagcaag cgctcgaaac ggtgcagcgg ctgttgccgg tgctgtgcca ggaccatggc     780
ctgaccccgg accaagtggt ggctatcgcc agcaacggtg cggcaagca agcgctcgaa      840 acggtgcagc ggctgttgcc ggtgctgtgc caggaccatg gcctgactcc ggaccaagtg     900
gtggctatcg ccagccacga tggcggcaag caagcgctcg aaacggtgca gcggctgttg     960
ccggtgctgt gccaggacca tggcctgact ccggaccaag tggtggctat cgccagccac    1020
gatggcggca agcaagcgct cgaaacggtg cagcggctgt tgccggtgct gtgccaggac    1080
catggcctga ccccggacca agtggtggct atcgccagca acattggcgg caagcaagcg    1140
ctcgaaacgg tgcagcggct gttgccggtg ctgtgccagg accatggcct gaccccggac    1200
caagtggtgg ctatcgccag caacaatggc ggcaagcaag cgctcgaaac ggtgcagcgg    1260
ctgttgccgg tgctgtgcca ggaccatggc ctgaccccgg accaagtggt ggctatcgcc    1320
agcaacggtg cggcaagca agcgctcgaa acggtgcagc ggctgttgcc ggtgctgtgc     1380
caggaccatg gcctgacccc ggaccaagtg gtggctatcg ccagcaacaa tggcggcaag    1440
caagcgctcg aaacggtgca gcggctgttg ccggtgctgt gccaggacca tggcctgacc    1500
ccggaccaag tggtggctat cgccagcaac attggcggca agcaagcgct cgaaagcatt    1560
gtggcccagc tgagccggcc tgatccggcg ttggccgcgt tgaccaacga ccacctcgtc    1620
gccttggcct gcctcggcgg acgtcctgcc atggatgcag tgaaaaaggg attgccgcac    1680
gcgccggaat tgatcagaag agtcaatcgc cgtattggcg aacgcacgtc ccatcgcgtt    1740
gcgatatcta gagtgggagg aagctctcgc agagagtcca tcaacccatg gattctgact    1800
ggtttcgctg atgccgaagg atcattcata ctagacatcc gcaaccgaaa caacgaaagc    1860
aacagatacc gaacttcgct gagattccag atcaccctgc acaacaagga caatcgatt     1920 ctggagaata tccagtccac ttggaaggtc ggcaagatca caaacagcag tgacagagcc    1980
gtcatgctga gggtcacccg tttcgaagat tgaaagtga ttatcgacca cttcgagaaa     2040
tatccgctga ttacccagaa attgggcgat tacaagttgt ttaaacaggc attcagcgtc    2100
atggagaata agaacatctt aaggagaat gggattaagg agctcgtacg aatcaaagct     2160
aagatgaatt ggggtctcaa tgacgaattg aaaaaagcat tccagagaa cattagcaaa     2220 gagcgccccc ttatcaataa gaacattccg aatttcaaat ggctggctgg attcacagct    2280
ggtgaaggct acttcggcgt gaatctaaaa aaggtaaagg gcaccgcaaa ggtatacgtg    2340
```

-continued

```
ggactgagat tctcaatctc acagcacatc agagacaaga acctgatgaa ttcattgata    2400
acatacctag gctgtggttc catctgggag aagaacaagt ctgagttcag atggctcgag    2460
ttcgtcgtaa ccaaattcag cgatatcaac gacaagatca ttccggtatt ccaggaaaat    2520
actctgattg gcgtcaaact cgaggacttt gaagattggt gcaaggttgc caaattgatc    2580
aaagagaaga acacctgac cgaatccggt ttggatgaga ttaagaaaat caagctgaac     2640
atgaacaaag gtcgtgtctt cgctagcacc ggttctgagc acctcgggc tgagaccttt     2700 gtattcctgg acctagaagc cactgggctc ccaaacatgg accctgagat tgcagagata    2760
tccctttttg ctgttcaccg ctcttccctg gagaacccag aacgggatga ttctggttcc    2820
ttggtgctgc cccgtgttct ggacaagctc acactgtgca tgtgcccgga gcgccccttt    2880
actgccaagg ccagtgagat tactggtttg agcagcgaaa gcctgatgca ctgcgggaag    2940
gctggtttca atggcgctgt ggtaaggaca ctgcagggct tcctaagccg ccaggagggc    3000
cccatctgcc ttgtggccca aatggcttc gattatgact tcccactgct gtgcacggag    3060
ctacaacgtc tgggtgccca tctgccccaa gacactgtct gcctggacac actgcctgca    3120
ttgcggggcc tggaccgtgc tcacagccac ggcaccaggg ctcaaggccg caaaagctac    3180
agcctggcca gtctcttcca ccgctacttc caggctgaac ccagtgctgc ccattcagca    3240
gaaggtgatg tgcacaccct gcttctgatc ttcctgcatc gtgctcctga gctgctcgcc    3300
tgggcagatg agcaggcccg cagctgggct catattgagc ccatgtacgt gccacctgat    3360
ggtccaagcc tcgaagcc                                                  3378
```

<210> SEQ ID NO 16
<211> LENGTH: 1126
<212> TYPE: PRT
<213> ORGANISM: artificial sequence
<220> FEATURE:
<223> OTHER INFORMATION: MegaTal TCRA_S02_Trex2

<400> SEQUENCE: 16

```
Met Gly Ser Cys Arg Tyr Pro Tyr Asp Val Pro Asp Tyr Ala Pro Pro
1               5                   10                  15

Lys Lys Lys Arg Lys Val Val Asp Leu Arg Thr Leu Gly Tyr Ser Gln
            20                  25                  30

Gln Gln Gln Glu Lys Ile Lys Pro Lys Val Arg Ser Thr Val Ala Gln
        35                  40                  45

His His Glu Ala Leu Val Gly His Gly Phe Thr His Ala His Ile Val
    50                  55                  60

Ala Leu Ser Gln His Pro Ala Ala Leu Gly Thr Val Ala Val Thr Tyr
65                  70                  75                  80

Gln His Ile Ile Thr Ala Leu Pro Glu Ala Thr His Glu Asp Ile Val
                85                  90                  95

Gly Val Gly Lys Gln Trp Ser Gly Ala Arg Ala Leu Glu Ala Leu Leu
            100                 105                 110

Thr Asp Ala Gly Glu Leu Arg Gly Pro Pro Leu Gln Leu Asp Thr Gly
        115                 120                 125

Gln Leu Val Lys Ile Ala Lys Arg Gly Gly Val Thr Ala Met Glu Ala
    130                 135                 140
```

-continued

```
Val His Ala Ser Arg Asn Ala Leu Thr Gly Ala Pro Leu Asn Leu Thr
145                 150                 155                 160

Pro Asp Gln Val Val Ala Ile Ala Ser Asn Ile Gly Gly Lys Gln Ala
                165                 170                 175

Leu Glu Thr Val Gln Arg Leu Leu Pro Val Leu Cys Gln Asp His Gly
            180                 185                 190

Leu Thr Pro Asp Gln Val Val Ala Ile Ala Ser Asn Ile Gly Gly Lys
        195                 200                 205

Gln Ala Leu Glu Thr Val Gln Arg Leu Leu Pro Val Leu Cys Gln Asp
210                 215                 220

His Gly Leu Thr Pro Asp Gln Val Val Ala Ile Ala Ser Asn Ile Gly
225                 230                 235                 240

Gly Lys Gln Ala Leu Glu Thr Val Gln Arg Leu Leu Pro Val Leu Cys
                245                 250                 255

Gln Asp His Gly Leu Thr Pro Asp Gln Val Val Ala Ile Ala Ser Asn
            260                 265                 270

Gly Gly Gly Lys Gln Ala Leu Glu Thr Val Gln Arg Leu Leu Pro Val
        275                 280                 285

Leu Cys Gln Asp His Gly Leu Thr Pro Asp Gln Val Val Ala Ile Ala
290                 295                 300

Ser His Asp Gly Gly Lys Gln Ala Leu Glu Thr Val Gln Arg Leu Leu
305                 310                 315                 320

Pro Val Leu Cys Gln Asp His Gly Leu Thr Pro Asp Gln Val Val Ala
                325                 330                 335

Ile Ala Ser His Asp Gly Gly Lys Gln Ala Leu Glu Thr Val Gln Arg
            340                 345                 350

Leu Leu Pro Val Leu Cys Gln Asp His Gly Leu Thr Pro Asp Gln Val
        355                 360                 365

Val Ala Ile Ala Ser Asn Ile Gly Gly Lys Gln Ala Leu Glu Thr Val
370                 375                 380

Gln Arg Leu Leu Pro Val Leu Cys Gln Asp His Gly Leu Thr Pro Asp
385                 390                 395                 400

Gln Val Val Ala Ile Ala Ser Asn Asn Gly Gly Lys Gln Ala Leu Glu
                405                 410                 415

Thr Val Gln Arg Leu Leu Pro Val Leu Cys Gln Asp His Gly Leu Thr
            420                 425                 430

Pro Asp Gln Val Val Ala Ile Ala Ser Asn Gly Gly Lys Gln Ala
        435                 440                 445

Leu Glu Thr Val Gln Arg Leu Leu Pro Val Leu Cys Gln Asp His Gly
450                 455                 460

Leu Thr Pro Asp Gln Val Val Ala Ile Ala Ser Asn Asn Gly Gly Lys
465                 470                 475                 480

Gln Ala Leu Glu Thr Val Gln Arg Leu Leu Pro Val Leu Cys Gln Asp
                485                 490                 495

His Gly Leu Thr Pro Asp Gln Val Val Ala Ile Ala Ser Asn Ile Gly
            500                 505                 510

Gly Lys Gln Ala Leu Glu Ser Ile Val Ala Gln Leu Ser Arg Pro Asp
        515                 520                 525

Pro Ala Leu Ala Ala Leu Thr Asn Asp His Leu Val Ala Leu Ala Cys
530                 535                 540

Leu Gly Gly Arg Pro Ala Met Asp Ala Val Lys Lys Gly Leu Pro His
545                 550                 555                 560
```

-continued

Ala Pro Glu Leu Ile Arg Arg Val Asn Arg Ile Gly Glu Arg Thr
                565                 570                 575

Ser His Arg Val Ala Ile Ser Arg Val Gly Ser Ser Arg Arg Glu
            580                 585                 590

Ser Ile Asn Pro Trp Ile Leu Thr Gly Phe Ala Asp Ala Glu Gly Ser
        595                 600                 605

Phe Ile Leu Asp Ile Arg Asn Arg Asn Asn Glu Ser Asn Arg Tyr Arg
    610                 615                 620

Thr Ser Leu Arg Phe Gln Ile Thr Leu His Asn Lys Asp Lys Ser Ile
625                 630                 635                 640

Leu Glu Asn Ile Gln Ser Thr Trp Lys Val Gly Lys Ile Thr Asn Ser
                645                 650                 655

Ser Asp Arg Ala Val Met Leu Arg Val Thr Arg Phe Glu Asp Leu Lys
            660                 665                 670

Val Ile Ile Asp His Phe Glu Lys Tyr Pro Leu Ile Thr Gln Lys Leu
        675                 680                 685

Gly Asp Tyr Lys Leu Phe Lys Gln Ala Phe Ser Val Met Glu Asn Lys
    690                 695                 700

Glu His Leu Lys Glu Asn Gly Ile Lys Glu Leu Val Arg Ile Lys Ala
705                 710                 715                 720

Lys Met Asn Trp Gly Leu Asn Asp Glu Leu Lys Lys Ala Phe Pro Glu
                725                 730                 735

Asn Ile Ser Lys Glu Arg Pro Leu Ile Asn Lys Asn Ile Pro Asn Phe
            740                 745                 750

Lys Trp Leu Ala Gly Phe Thr Ala Gly Glu Gly Tyr Phe Gly Val Asn
        755                 760                 765

Leu Lys Lys Val Lys Gly Thr Ala Lys Val Tyr Val Gly Leu Arg Phe
    770                 775                 780

Ser Ile Ser Gln His Ile Arg Asp Lys Asn Leu Met Asn Ser Leu Ile
785                 790                 795                 800

Thr Tyr Leu Gly Cys Gly Ser Ile Trp Glu Lys Asn Lys Ser Glu Phe
                805                 810                 815

Arg Trp Leu Glu Phe Val Val Thr Lys Phe Ser Asp Ile Asn Asp Lys
            820                 825                 830

Ile Ile Pro Val Phe Gln Glu Asn Thr Leu Ile Gly Val Lys Leu Glu
        835                 840                 845

Asp Phe Glu Asp Trp Cys Lys Val Ala Lys Leu Ile Lys Glu Lys Lys
    850                 855                 860

His Leu Thr Glu Ser Gly Leu Asp Glu Ile Lys Lys Ile Lys Leu Asn
865                 870                 875                 880

Met Asn Lys Gly Arg Val Phe Ala Ser Thr Gly Ser Glu Pro Pro Arg
                885                 890                 895

Ala Glu Thr Phe Val Phe Leu Asp Leu Glu Ala Thr Gly Leu Pro Asn
            900                 905                 910

Met Asp Pro Glu Ile Ala Glu Ile Ser Leu Phe Ala Val His Arg Ser
        915                 920                 925

Ser Leu Glu Asn Pro Glu Arg Asp Asp Ser Gly Ser Leu Val Leu Pro
    930                 935                 940

Arg Val Leu Asp Lys Leu Thr Leu Cys Met Cys Pro Glu Arg Pro Phe
945                 950                 955                 960

Thr Ala Lys Ala Ser Glu Ile Thr Gly Leu Ser Ser Glu Ser Leu Met
                965                 970                 975

His Cys Gly Lys Ala Gly Phe Asn Gly Ala Val Val Arg Thr Leu Gln

-continued

```
            980             985             990
Gly Phe Leu Ser Arg Gln Glu Gly Pro Ile Cys Leu Val Ala His Asn
        995                1000                1005

Gly Phe Asp Tyr Asp Phe Pro Leu Leu Cys Thr Glu Leu Gln Arg Leu
        1010               1015                1020

Gly Ala His Leu Pro Gln Asp Thr Val Cys Leu Asp Thr Leu Pro Ala
1025               1030                1035                1040

Leu Arg Gly Leu Asp Arg Ala His Ser His Gly Thr Arg Ala Gln Gly
                 1045                1050                1055

Arg Lys Ser Tyr Ser Leu Ala Ser Leu Phe His Arg Tyr Phe Gln Ala
                1060                1065                1070

Glu Pro Ser Ala Ala His Ser Ala Glu Gly Asp Val His Thr Leu Leu
        1075                1080                1085

Leu Ile Phe Leu His Arg Ala Pro Glu Leu Leu Ala Trp Ala Asp Glu
        1090                1095                1100

Gln Ala Arg Ser Trp Ala His Ile Glu Pro Met Tyr Val Pro Pro Asp
1105               1110                1115                1120

Gly Pro Ser Leu Glu Ala
                1125
```

LAGLIDADG HOMING ENDONUCLEASE CLEAVING THE T CELL RECEPTOR ALPHA GENE AND USES THEREOF

SEQUENCE LISTING

The instant application contains a Sequence Listing which has been filed electronically in ASCII format and is hereby incorporated by reference in its entirety. Said ASCII copy, created on Nov. 16, 2017, is named P81303518US00_repl.txt and is 58,411 bytes in size.

FIELD OF THE INVENTION

The present disclosure relates to molecular and cellular biology, genetics, genomics, and their applications in human therapeutics. Particular aspects relate to a rare-cutting endonuclease cleaving a nucleic acid target sequence from the TCR-alpha gene, more particularly to a new meganuclease variant of I-Onul or homologues that is particularly efficient in disrupting the expression of this gene in T-cells, and the use thereof for cancer therapy.

BACKGROUND OF THE INVENTION

Site-specific nucleases are powerful reagents for specifically and efficiently targeting and modifying a DNA sequence within a complex genome. The double-stranded DNA breaks caused by site-specific nucleases are commonly repaired through the distinct mechanisms of homologous recombination or non-homologous end joining (NHEJ). Although homologous recombination typically uses the sister chromatid of the damaged DNA as a donor matrix from which to perform perfect repair of the genetic lesion, NHEJ is an imperfect repair process that often results in changes to the DNA sequence at the site of the double strand break. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. There are numerous applications of genome engineering by site-specific nucleases extending from basic research to bioindustrial applications and human therapeutics. Re-engineering a DNA-binding protein for this purpose has been mainly limited to the naturally occurring LADLIDADG homing endonuclease (LHE), artificial zinc finger proteins (ZFP), the Transcription Activator Like Effectors nucleases (TALE-nucleases), and the recently described CRISPR-Cas system.

Homing endonucleases, also known as meganucleases, are sequence-specific endonucleases with large (>14 bp) cleavage sites that can deliver DNA double-strand breaks at specific loci (Thierry and Dujon 1992). There are a handful of known homing endonuclease families which are demarcated on the basis of canonical motifs and the structural features which comprise them. However, they all share the property of recognizing and cleaving long DNA targets. Homing endonucleases were the first, and to date only, naturally occurring endonucleases with specificities at or approaching 'genome level', meaning having putative target sequences that occur very infrequently, or perhaps singularly, in their host genome. As a general property, HEs have a moderate degree of fidelity to their DNA target sequences, such that most base pair substitutions to their DNA target sequences reduce or eliminate the ability of the HE to bind or cleave it. HEs are therefore the most specific naturally occurring endonucleases yet discovered, and indeed this property is critical to the natural life cycle of the genetic elements in which they are encoded.

Homing endonuclease genes (HEGs) are classified as a type of selfish genetic element, as their DNA recognition and cleavage activity can lead to a DNA repair event that results in the copying of the HEG into the cleavage site. This mechanism of horizontal gene transfer, referred to as 'homing' results in a super-Mendelian inheritance pattern. Using this mechanism, HEGs and their endonuclease gene products can spread rapidly within their host species populations, and have also spread throughout all kingdoms of life over evolutionary time. HEGs are most commonly found in highly conserved genomic locations that do not impart fitness costs on their host organisms, such as within introns or as non-disruptive N- or C-terminal fusions to host proteins.

The LAGLIDADG homing endonuclease family (LHE) comprises a group of compact (<320 amino acids) nucleases whose structural and mechanistic properties have been studied extensively owing to their attractive properties for genome engineering applications. LHEs operate either as dimers or as pseudo-dimeric monomers, with the DNA cleaving active site occurring at the DNA-facing end of the interface of the two subunits (in dimeric LHEs) or domains (in monomeric LHEs). The LAGLIDADG consensus motifs for which LHEs are named are found in the two central alpha helices which form this interface between the two subunits or domains. At the bottom of each LAGLIDADG helix are the residues which together coordinate the hydrolysis reaction if the appropriate conditions are met, such as if the LHE finds and binds to an appropriate DNA target sequence. The active site covers the 'central-4' DNA bases of the DNA target sequence.

On either side of the active site are the two DNA binding domains LHEs use to recognize their DNA target sequences. Each domain comprises an anti-parallel beta sheet which wraps around nearly a complete turn of DNA and contacts 9 base pairs of DNA sequence. Members of the LHE family thus recognize 22 base pair DNA target sequences (9 base pairs for each domain, and 4 base pairs covered by the active site), which are partially palindromic in the case of dimeric LHEs, but can be entirely asymmetric for monomeric LHEs. Emanating from each anti-parallel beta sheet are the amino acid side chains which comprise the DNA recognition interface. While there is much amino acid conservation throughout the non-DNA interfacing residues amongst the LHE family, DNA recognition interface amino acid compositions vary significantly. This is because for each LHE the DNA recognition interface comprises an extensive network of side chain-to-side chain and side chain-to-DNA contacts, most of which is necessarily unique to a particular LHE's DNA target sequence. The amino acid composition of the DNA recognition interface (and the correspondence of it to a particular DNA sequence) is therefore the definitive feature of any natural or engineered LHE. The DNA recognition interface functions in determining the identity of the DNA target sequence which can be accommodated and hydrolyzed and also the affinity and specificity properties which define the quality of the LHE according to the demands of the application.

Owing to their small size and exquisite specificity properties, LHEs have been the subject of numerous efforts to engineer their DNA recognition properties with the desired outcome of cleaving and altering genes of interest in research, biotechnology, crop science, global health, and human therapeutics applications. However, the extent of the networks of residues which form the DNA recognition interface has generally prevented efficient methods for re-addressing LHEs to DNA target sequences of interest. This has led to continued innovation in field of gene-specific nuclease engineering, with three endonuclease alternative platforms now validated as having the capacity to target DNA sequences with ranging (but generally high) levels of specificity, as well as new and improved methods for overcoming the challenges of engineering the DNA recognition interfaces of LHEs.

Zinc finger nucleases (ZFNs) generating by fusing a plurality of Zinc finger-based DNA binding domains to an independent catalytic domain (Kim, Cha et al. 1996; Smith, Berg et al. 1999; Smith, Bibikova et al. 2000) represent another type of engineered nuclease commonly used to stimulate gene targeting and have been successfully used to induce gene correction, gene insertion and gene deletion in research and therapeutic applications. The archetypal ZFNs are based on the catalytic domain of the Type IIS restriction enzyme FokI and Zinc Finger-based DNA binding domains made of strings of 3 or 4 individual Zinc Fingers, each recognizing a DNA triplet (Pabo, Peisach et al. 2001). Two Zinc Finger-FokI monomers have to bind to their respective Zinc Finger DNA-recognition sites on opposite strands in an inverted orientation in order to form a catalytically active dimer that catalyze double strand cleavage (Bitinaite, Wah et al. 1998).

Transcription activator-like effectors (TALEs) were the next artificial endonuclease platform. TALEs derived from a family of proteins used in the infection process by plant pathogens of the *Xanthomonas* or *Ralstonia* genus are repetitive proteins characterized by 14-20 repeats of 33-35 amino acids differing essentially by two positions. Each base pair in the DNA target is contacted by a single repeat, with the specificity resulting from the two variant amino acids of the repeat (the so-called repeat variable dipeptide, RVD). The apparent modularity of these DNA binding domains has been confirmed to a certain extent by modular assembly of designed TALE-derived protein with new specificities (Boch, Scholze et al. 2009; Moscou and Bogdanove 2009). Very similarly to ZFNs, TALEs were readily adapted into site-specific nucleases by arraying TALE repeats with RVDs corresponding to the target sequence of choice and fusing the resultant array to a FokI domain. As such, DNA cleavage by a TALE-Nuclease requires two DNA recognition regions flanking an unspecific central region. TALE nucleases have proliferated widely since 2010 owing to their ease of production and improved double-strand break generating efficiency.

Of these distinct technologies, it is important to distinguish the advantaged properties of each and to determine innovative ways to capture these properties for the appropriate genome engineering applications. One of the most powerful applications of site-specific nuclease technology is in the field of human therapeutics, which requires the use of highly efficient and specific nuclease reagents to safely and effectively edit genomic information in human cells or tissues. A one prominent example is the cancer immunotherapy field, which is at the forefront of applying nuclease technological advances for developing novel therapeutics. These approaches are focused on harnessing the powerful anti-tumor activities of patient-derived (autologous) or donor-derived (allogeneic) T-cells and leveraging this potential via genome engineering of cell-intrinsic properties such as cellular proliferation, engraftment, migration or longevity. Successful and scalable manufacture of T-cells endowed with enhanced anti-cancer activity requires generation of highly efficient nuclease compositions and simplified delivery strategies, such as those described in some aspects of this application.

The immune system has a key foundational role in detecting and preventing the development of human cancer. The majority of transformed cells are quickly detected by immune sentinels and destroyed through the activation of antigen-specific T-cells via clonally expressed T-cell receptors (TCR). Oncogenesis is thus an immunological disorder, a failure of immune system to mount the necessary anti-tumor response to durably suppress and eliminate the disease. Certain immunotherapy interventions developed over the last few decades, such as recombinant cytokine infusions, have specifically focused enhancing T-cell immunity, and while these have been associated with sporadic cases of disease remission, they have not had substantial overall success. Recent therapies with monoclonal antibodies targeting molecules which inhibit T-cell activation, such as CTLA-4 or PD-1, have shown a more substantial anti-tumor effect, however these treatments are associated with substantial toxicity due to systemic immune activation. Most recently, therapeutic strategies which are based on the isolation, modification, expansion and reinfusion of T-cells have been explored and tested in early stage clinical trials. These treatments have shown mixed rates of success, but a number of patients have experienced unprecedented objective responses and durable remissions, highlighting the potential for T-cell based cancer immunotherapies. Genome editing strategies which are designed to harness this potential for successful widespread implementation of T-cell cancer immunotherapies are described herein.

Successful recognition of tumor cell associated antigens by cytolytic T-cells initiates targeted tumor lysis and underpins any effective cancer immunotherapy approach. Some tumors contain tumor-infiltrating T-cells (TILs) which express TCRs specifically directed tumor-associated antigens; however access to substantial numbers of TILs is limited to only a few human cancers. In response to this limitation, artificial antigen recognition and signaling transgenes called chimeric antigen receptors (CARs) have been devised to broaden the scope and utility of T-cell based cancer immunotherapy. CARs are transmembrane spanning proteins whose extracellular portions contain antigen recognition domains most typically derived from single-chain variable fragments (scFv) of monoclonal antibodies, and whose intracellular domains contain combinations of signaling domains to mimic TCR-like activation signals. It has been widely demonstrated that primary human T-cells made to express CARs are able to respond to and kill cells which bear the antigen recognized by the scFv domain.

Despite highly promising initial results with CAR-expressing transgenic T-cells, the efficacy, safety and scalability of CAR-based T-cell immunotherapies is limited by continuous expression of clonally derived TCR. Residual TCR expression may interfere with CAR signaling in engineered T-cells or it may initiate off-target and pathologic responses to self- or allo-antigens. Consequently, CAR-based T-cells have only been used in autologous applications. Genetic abolition of endogenous TCR through nuclease-mediated gene editing would reduce the risk of damaging collateral responses and decrease the potential for T-cell mediated graft vs. host disease (GVHD). The main hurdle for developing universal allogeneic T-cell therapy is the development of GVHD through the activation of donor T cells' TCR by the recipients' HLA complex. Removal of the TCR would prevent such graft-versus-host responses and enable the development of simple and widely applicable allogeneic T-cell therapies.

In addition to cancer, T-cell therapies are being developed for a wide range of therapeutic applications including chronic viral infections, autoimmune disease and stem cell transplantation. In disease models and initial clinical models have shown a key role for the regulatory T cell subset (T-regs) in controlling the development and extent of GVHD and various autoimmune diseases. Transfer of regulatory T cells ameliorates GVHD in patients receiving stem cell transplant. In addition, transfer of regulatory T cells improved disease outcome in preclinical models of rheumatoid arthritis, type-1 diabetes and systemic lupus erythematosus, amongst others. This approach is also being tested in patients with chronic viral infections such as Hepatitis B (HBV). Engineered T cells containing HBV-specific CARs are highly active against HBV-infected cells. These approaches are being tested in clinical trials, however their use is limited by the same manufacturing and scalability hurdles associated with other autologous therapies. Combining genetic targeting of TCR-alpha in T cells with CARs targeting tolerance or viral targets represents a very powerful way to develop allogeneic T cell therapy for the treatment of human disease.

SUMMARY OF THE INVENTION

A genome engineering strategy to generate therapeutic T-cell products, such as in the treatment of human diseases, requires the use of safe and effective endonuclease reagents for disrupting TCR-alpha gene. The endonuclease I-Onul, encoded within a group I intron in the Rps3 host gene from *Ophiostoma novo-ulmi* subsp *americana*, and its closely related homologs, have been recently characterized to be monomeric proteins displaying the characteristics of the LAGLIDADG homing endonucleases and to be sufficiently active for use in genome editing (WO2011/156430, (Sethuraman, Majer et al. 2009; Takeuchi, Lambert et al. 2011)).

In particular aspects, several I-Onul variants were created in an attempt to target different DNA sequences in the TCR-alpha gene. In additional aspects, new LHE variant targeting the constant domain of the TCR-alpha gene are provided. This particular I-Onul variant showed high efficiency in disrupting the expression of TCR-alpha in T-cells. In further aspects, this particular variant of the invention were then fused to some engineered nucleic acid binding domains, so as to form chimeric endonucleases that also showed improved properties, especially increases in specificity and efficiency which are required for obtaining safe and useful reagents for treating primary human cells. These molecules have proven efficiency for genome editing at the TCR-alpha locus and will be useful in numerous T-cell based methods for treating human disease.

BRIEF DESCRIPTION OF THE FIGURES

For a better understanding of the invention and to show how the same may be carried into effect, there will now be shown by way of example only, specific embodiments, methods and processes according to the present invention with reference to the accompanying drawings in which:

FIG. 5 shows a comparative alignment of the TCRA_S02_2E5 variant (SEQ ID NO: 6) and its derivative, TCRA_S02_RD2_8 (SEQ ID NO: 10), which was identified on the second round of activity refinement. The strand-loop-strand motifs which comprise the DNA binding domain are depicted above the aligned sequences.

FIG. 8 shows the flow cytometry scatter properties of primary human T cells which are highly susceptible to double-stranded DNA breaks resulting in genotoxicity and cell death. T cells transfected with IVT-mRNA species encoding an innocuous protein such as the blue fluorescent protein (BFP), show 59% survival during in vitro culture, a level similar to unmanipulated T cells. The TCRA_S02_2E5_RD2_8 variant results in very similar levels of T cell viability, confirming that its global DNA specificity is of high quality.

FIG. 16 shows the positions of the amino acid residues in the TCRA S02-targeting LHE that were varied or otherwise became altered relative to the primary sequence of the wild-type I-*Onul* protein during the re-specification process. The TCRA S02 2E5 LHE contains variations only to the 44 residues which comprise the protein-DNA interface, not all of which retuned amino acids different from the wild-type I-Onul protein, but all of which were varied in the initial stages of respecification. The top performing variant following refinement screening had additional six mutations, 5 of which are located within the protein-DNA interface, 1 of which is elsewhere in the protein.

DETAILED DISCLOSURE OF THE INVENTION

Figure 1:
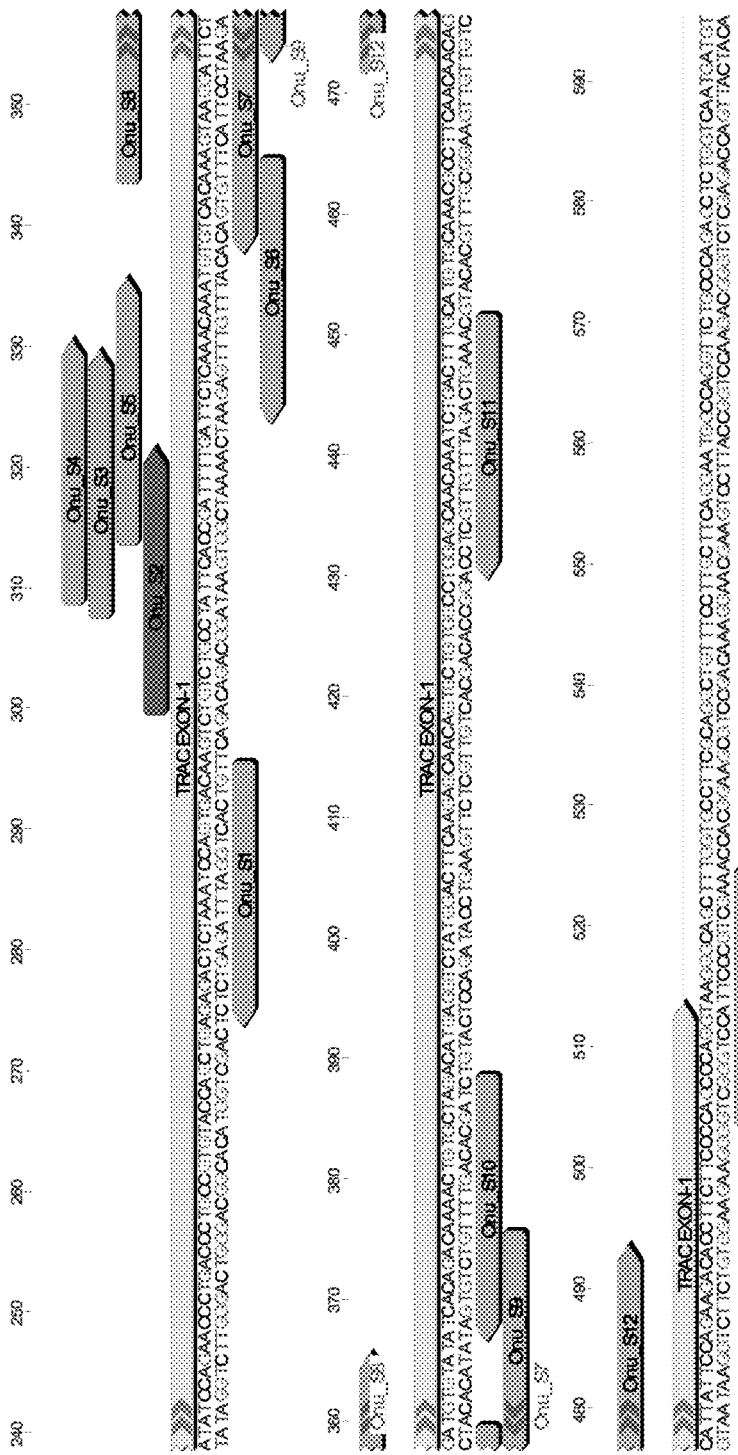
FIG. 1: depicts the location of thirteen putative target sequences, annotated as Onu_S##, in the first exon of the human TRAC gene (SEQ ID NOs: 17 and 18) for which superior LHE-DNA recognition sequences are predicted. The location of the first exon of the TRAC gene is indicated.

Unless specifically defined herein, all technical and scientific terms used have the same meaning as commonly understood by a skilled artisan in the fields of gene therapy, biochemistry, genetics, molecular biology and immunology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

I-OnuI and I-OnuI Homologues Variants

The present invention relates to rare-cutting endonucleases involving I-OnuI variants and I-OnuI homologues variants of I-LtrI, I-LtrWI, I-PanMI, I-PanMII, I-PanMIII, I-GzeI, I-GzeMII, I-GzeMIII, I-GpiI, I-GpeMI, I-AabMI, I-AaeMI, I-ApaMI, I-CpaMI, I-CpaMII, I-CpaMIII, I-CpaMIV, I-CpaMV, I-EjeMI, I-CkaMI, I-CraMI, I-MpeMI, I-MveMI, I-NcrMI, I-OheMI, I-OsoMI, I-OsoMII, I-OsoMIII, I-OsoMIV, I-SmaMI, I-SscMI, I-Vdi141I, I-PnoMI, I-ScuMI; (Takeuchi, Lambert et al. 2011) in which mutations have been introduced and able to that specifically target a nucleic acid sequence present in the TRAC gene.

The rare-cutting endonucleases according to the present invention refer to variant enzymes capable of catalyzing the hydrolysis (cleavage) of bonds between nucleic acids within a DNA or RNA molecule, preferably a DNA molecule. The endonucleases according to the present invention recognize and cleave nucleic acids at specific polynucleotide sequences, further referred to as the "nucleic acid target sequence".

To engineer rare-cutting endonucleases specific for target sites in the TRAC gene, the inventors constructed libraries of I-OnuI variants in which amino acid residues localized in the DNA recognition interface of natural I-OnuI were varied. The libraries were screened for target cleavage activity against each predicted TRAC target sites using previously described cleavage assays (Jarjour, West-Foyle et al. 2009). The specificity of the DNA recognition interface of I-OnuI was thus altered to target sequences present in the human TRAC gene.

By "variant(s)", is meant a protein or a polynucleotide encoding thereof that do not naturally exist in nature and that are obtained by genetic engineering or by random mutagenesis. I-OnuI or I-OnuI homologue variants according to the invention can for example be obtained by deletion or substitution with a different amino acid of at least one residue in the amino acid sequence of their wild-type sequences. Substitution(s) and deletions can for example be introduced by directed mutagenesis and/or by random mutagenesis. In the frame aspects of the present invention, I-OnuI or I-OnuI homologues variants have the ability to target TRAC gene, which mean that they can interact with some specific DNA sequences encoding said gene.

The variants or homologues according to the invention comprise the DNA recognition interface as described herein and as provided in FIG. 16.

A DNA recognition interface refers to the residues of the protein domains of homing endonuclease or variant thereof which interact with nucleic acid target bases as well as those residues that are adjacent. For each homing endonuclease, the DNA recognition interface comprises an extensive network of side chain-to-side chain and side chain-to-DNA contacts, most of which is necessarily unique to recognize a particular nucleic acid target sequence. Thus, the DNA recognition interface amino acid compositions (and the correspondence of it to a particular nucleic acid sequence) vary significantly and is therefore the definitive feature of any natural or engineered homing endonuclease. The DNA recognition interface determines the identity of the nucleic acid target sequence and also the affinity and specificity properties which define the quality of the homing endonuclease according to the demands of the application.

According to the present invention, the I-OnuI or I-OnuI homologue variants comprise one or more substitutions in the DNA recognition interface. Accordingly, the I-OnuI variant or homologue according to the present invention has at least 70%, more preferably at least 75%, more preferably at least 80%, more preferably at least 85%, more preferably at least 90%, more preferably at least 95%, more preferably at least 97%, more preferably at least 99% sequence identity with the DNA recognition interface of I-OnuI (Takeuchi, Lambert et al. 2011).

In a particular embodiment, said I-OnuI or I-OnuI homologue variants comprise one or more substitution(s) and/or mutations in the DNA recognition interface, particularly in the subdomains situated from positions 24-50, 68 to 82, 180 to 203 and 223 to 240 of I-OnuI (SEQ ID NO: 2). The I-OnuI variant or homologue can also comprise one or more substitutions at additional positions situated anywhere within the entire I-OnuI sequence. The residues which are substituted and/or mutated may include residues contacting the nucleic acid target or interacting with the nucleic acid backbone or with the nucleotide bases, directly or via a water molecule as described in Takeuchi, Lambert et al. 2011.

For example, said I-OnuI variant comprises one or more substitutions and/or mutations, preferably at least 10, preferably at least 15, more preferably at least 20, even more preferably at least 25 in at least one position selected from the position group consisting of positions: 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, 240 of I-OnuI (SEQ ID NO: 2). In particular embodiments, said substitutions and/or mutations are replacement of at least one of the initial amino acids, in each case with an amino acid selected from the group consisting of: A, D, E, G, H, K, N, P, Q, R, S, T, Y, C, V, L, W, M and I.

As non limiting examples, the leucine (L) at position 26 may be replaced by/mutated to isoleucine (I); the arginine at position 28 may be replaced by/mutated to aspartic acid (D), the asparagine (N) at position 32 may be replaced by/mutated to arginine (R); the lysine (K) at position 34 may be replaced by/mutated to asparagine (N); the serine (S) at position 35 may be replaced by/mutated to glutamic acid (E); the valine (V) at position 37 may be replaced by/mutated to asparagine (N); the glycine (G) at position 38 may be replaced by/mutated to arginine (R); the serine (S) at position 40 may be replaced by/mutated to arginine (R); the glutamic acid (E) at position 42 may be replaced by/mutated to serine (S); the glycine (G) at position 44 may be replaced by/mutated to arginine (R) (see FIG. 16).

The valine (V) at position 68 may be replaced by/mutated to lysine (K); the alanine (A) at position 70 may be replaced by/mutated to threonine (T); the asparagine (N) at position 75 may be replaced by/mutated to arginine (R); the serine (S) at position 78 may be replaced by/mutated to methionine (M); the lysine (K) at position 80 may be replaced by/mutated to arginine (R) (see FIG. 16).

The leucine (L) at position 138 may be replaced by/mutated to methionine (M); the serine (S) at position 159 may be replaced by/mutated to proline (P); The glutamic acid (E) at position 178 may be replaced by/mutated to aspartic acid (D); the cysteine (C) at position 180 may be replaced by/mutated to tyrosine (Y); the phenylalanine (F) at position 182 may be replaced by/mutated to glycine (G); the isoleucine (I) at position 186 may be replaced by/mutated to lysine (K); the serine (S) at position 188 may be replaced by/mutated to valine (V); the serine (S) at position 190 may be replaced by/mutated to glycine (G); the lysine (K) at position 191 may be replaced by/mutated to asparagine (N); the leucine (L) at position 192 may be replaced by/mutated to alanine (A); the glycine (G) at position 193 may be replaced by/mutated to lysine (K); the glutamine (Q) at position 195 may be replaced by/mutated to tyrosine (Y); the glutamine (Q) at position 197 may be replaced by/mutated to glycine (G); the valine (V) at position 199 may be replaced by/mutated to arginine (R); the threonine (T) at position 203 may be replaced by/mutated to serine (S); the lysine (K) at position 207 may be replaced by/mutated to arginine (R) (see FIG. 16)

The tyrosine (Y) at position 223 may be replaced by/mutated to serine (S); the lysine (K) at position 225 may be replaced by/mutated to tryptophan (W); the aspartic acid (D) at position 236 may be replaced by/mutated to glutamic acid (E) (see FIG. 16).

In a more preferred embodiment the I-Onul variant comprise the protein sequence selected from the group consisting of SEQ ID NO: 6, SEQ ID NO: 8, and SEQ ID NO: 10.

In a preferred embodiment, the I-Onul or I-Onul homologue variant according to the present invention has at least 70%, more preferably at least 75%, more preferably at least 80%, more preferably at least 85%, more preferably at least 90%, more preferably at least 95%, more preferably at least 97%, more preferably at least 99% sequence identity with the protein sequence SEQ ID NO: 6, SEQ ID NO: 8, and SEQ ID NO: 10.

According to a preferred embodiment of the invention the I-Onul or I-Onul homologues variants according to the invention cleave a target sequence that is different from the target sequence of the corresponding wild-type endonuclease. Cleavage in the nucleic acid target sequence can correspond to either a double-stranded break or a single-stranded break The present invention is based on the finding that such variant endonucleases with novel specificities can be used to allow efficient targeted modification of the TRAC gene.

The present inventors have indeed identified putative I-Onul target sequences in the human TRAC gene based on a series of common features intrinsic to the group of monomeric I-Onul-like LHE subfamily members recently described in (Takeuchi, Lambert et al. 2011; Baxter, Lambert et al. 2012). The putative LHE target sequences are also identified on the basis of the locations within TRAC gene wherein endonuclease-mediated insertions or deletions can cause significant disruptions to the TCR-alpha protein. The present inventors identified two putative target sequences in the human TRAC gene (SEQ ID NO: 3 to SEQ ID NO: 4) upon which the DNA recognition interface of the I-Onul variants were engineered. Among these two putative target sites, one sequence (TCRA_S02) has been successfully targeted by the resulting I-Onul variants.

Accordingly, the present invention relates to a rare-cutting endonuclease comprising an I-Onul or I-Onul homologue variant that recognizes a target nucleic acid sequence present within TRAC gene, preferably those present in the exon 1 of the TRAC gene, more preferably a target nucleic acid sequence comprising nucleic acid sequence SEQ ID NO: 3

Chimeric Endonuclease

In another aspect, the invention relates to a rare-cutting endonuclease under the form of a chimeric endonuclease comprising an I-Onul or I-Onul homologue variant as described above, optionally fused to at least one additional protein domain by a peptide linker. The additional protein domain may be selected from the group consisting of: a nucleic acid binding domain to allow higher specificity on target nucleic acid sequence and avoid off target site; a catalytic domain to process (eg. polymerize, depolymerize, modify) target nucleic acid sequence; and one or more terminal epitope tags or fluorescent proteins to follow and visualize the chimeric protein.

In a particular embodiment, the I-Onul or I-Onul homologue variant is fused to a nucleic acid binding domain such as TALE nucleic acid binding domain as non-limiting example to improve TRAC gene targeting.

Said Transcription Activator like Effector (TALE) corresponds to an engineered TALE comprising a plurality of TALE repeat sequences, each repeat comprising a RVD specific to each nucleotide base of a TALE recognition site. In the present invention, each TALE repeat sequence of said TALE is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 particularly in TALE repeat sequence larger than 33 or 34 amino acids long. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. By other amino acid residues is intended any of the twenty natural amino acid residues or unnatural amino acids derivatives.

In another embodiment, said TALE of the present invention comprises between 5 and 30 TALE repeat sequences. More preferably, said TALE of the present invention comprises between 8 and 20 TALE repeat sequences; again more preferably 10 TALE repeat sequences.

In another embodiment, said TALE comprises an additional single truncated TALE repeat sequence made of 20 amino acids located at the C-terminus of said set of TALE repeat sequences, i.e. an additional C-terminal half-TALE repeat sequence. In this case, said TALE of the present invention comprises between 5.5 and 30.5 TALE repeat sequences, "0.5" referring to previously mentioned half-TALE repeat sequence (or terminal RVD, or half-repeat). More preferably, said TALE of the present invention comprises between 5.5 and 20.5 TALE repeat sequences, again more preferably, 10.5 TALE repeat sequences. In a preferred embodiment, said half-TALE repeat sequence is in a TALE context which allows a lack of specificity of said half-TALE repeat sequence toward nucleotides A, C, G, T. In a more preferred embodiment, said half-TALE repeat sequence is absent. In another embodiment, said TALE of the present invention comprises TALE like repeat sequences of different origins. In a preferred embodiment, said TALE comprises TALE like repeat sequences originating from different naturally occurring TAL effectors. In another preferred embodiment, internal structure of some TALE like repeat sequences of the TALE of the present invention are constituted by structures or sequences originated from different naturally occurring TAL effectors. In another embodiment, said TALE of the present invention comprises TALE like repeat sequences. TALE like repeat sequences have a sequence different from naturally occurring TALE repeat sequences but have the same function and/or global structure within said core scaffold of the present invention.

The chimeric endonuclease according to the invention can therefore correspond to the fusion of I-Onul variant or I-Onul homologue variant as previously described to a modular nucleic acid binding domain, such as a TALE or a zinc-finger domain, said fusion being active under monomeric form, as part as a single chain polypeptide.

According to a further aspect of the invention, the protein domain fused to the I-Onul variant or I-Onul homologue variant may have at least one catalytical activity selected from the group consisting of nuclease activity, polymerase activity, kinase activity, phosphatase activity, methylase activity, topoisomerase activity, integrase activity, transposase activity, ligase activity, helicase activity, recombinase activity. In a preferred embodiment, protein domain has an endonuclease activity, whereas the Onu-1 variant retains its own cleavage activity or solely retains binding affinity to TRAC; in another preferred embodiment, said protein domain is or comprises an exonuclease activity. As non-limiting examples, As non-limiting examples, catalytic domains may be or comprise in part one of the proteins selected in the group consisting of: MmeI, Colicin-E7 (CEA7_ECOLX), Colicin-E9, APFL, EndA, Endo I (END1_ECOLI), Human Endo G (NUCG_HUMAN), Bovine Endo G (NUCG_BOVIN), R.HinPlI, I-BasI, I-BmoI, I-HmuI, I-TevI, I-TevII, I-TevIII, I-TwoI, R.MspI, R.MvaI, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD6I (R.BspD6I large subunit), ss.BspD6I (R.BspD6I small subunit), R.PleI, MlyI, AlwI, Mva1269I, BsrI, BsmI, Nb.BtsCI, Nt.BtsCI, R1.BtsI, R2.BtsI, BbvCI subunit 1, BbvCI subunit 2, Bpu10I alpha subunit, Bpu10I beta subunit, BmrI, BfiI, I-CreI, hExoI (EXO1_HUMAN), Yeast ExoI (EXO1_YEAST), *E. coli* ExoI, Human TREX2, Mouse TREX1, Human TREX1, Bovine TREX1, Rat TREX1, Human DNA2, Yeast DNA2 (DNA2_YEAST), TdT and VP16 or a functional mutant thereof.

In a preferred embodiment, the catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, phosphatase, hydrolases and template-independent DNA polymerases. In a more preferred embodiment, said catalytic domain has an exonuclease activity, in particular a 3'-5' exonuclease activity. In a more preferred embodiment, said catalytic domain is TREX2 or a functional variant thereof. In another preferred embodiment, said catalytic domain is encoded by a single chain TREX2 polypeptide. In a particular embodiment, said catalytic domain is fused to the N-terminus or C-terminus of said rare-cutting endonuclease. In a more preferred embodiment, said catalytic domain is fused to said rare-cutting endonuclease by a peptide linker.

In particular aspects, peptide linkers act as a communication device/linking or joining element between the rare-cutting endonuclease and an additional protein domain to act in concert for activity. Said peptide linker provides a peptide sequence which allows the connection of different monomers in a fusion protein and the adoption of the correct conformation for said fusion protein activity, but does not alter the specificity of either of the monomers for their targets. Peptide linkers can be of various sizes, from 2 amino acids to 50 amino acids as a non-limiting indicative range. Peptide linkers can also be structured or unstructured.

Alternatively, the I-Onul variant or I-Onul homologue variant according to the invention is used in conjunction with another protein not being fused thereto, having the same catalytic activity as the protein domain described above.

Another aspect of the invention provides polynucleotides comprising nucleic acid sequence encoding the rare-cutting endonucleases, preferably I-Onul variants, homologues or chimeric endonuclease as described herein and vectors comprising such polynucleotides. Nucleic acid or vectors according to additional aspects of the present invention can comprise a nucleic acid sequence encoding one or more subcellular localization motifs, protease cleavage sites or ribosomal skip sequences.

In particular embodiments, the nucleic acids of the present invention can comprise at least one subcellular localization motif. A subcellular localization motif refers to a sequence that facilitates transporting or confining a protein to a defined subcellular location that includes at least one of the nucleus, cytoplasm, plasma membrane, endoplasmic reticulum, golgi apparatus, endosomes, peroxisomes and mitochondria. Subcellular localization motifs are well-known in the art. Subcellular localization motif requires a specific orientation, e.g., N- and/or C-terminal to the protein. As a non-limiting example, the nuclear localization signal (NLS) of the simian virus 40 large T-antigen can be oriented at the N and/or C-terminus. NLS is an amino acid sequence which acts to target the protein to the cell nucleus through Nuclear Pore Complex and to direct a newly synthesized protein into the nucleus via its recognition by cytosolic nuclear transport receptors. Typically, a NLS consists of one or more short sequences of positively charged amino acids such as lysines or arginines.

Methods of Genome Engineering

Another aspect of the invention concerns the use of I-Onul variant, I-Onul homologue variant or I-Onul derived chimeric endonuclease as described above to allow efficient TRAC gene targeting in a cell. More particularly, the invention relates to a method for targeted modification in the TRAC gene in a cell comprising introducing into a cell the rare-cutting endonuclease or chimeric endonuclease as described above. In a particular embodiment, the present invention relates to a method for modifying the TRAC gene in a cell comprising, introducing into the cell the rare-cutting endonuclease more particularly the I-OnuI variant, I-OnuI homologue variant or chimeric endonuclease, such that the rare-cutting endonuclease cleaves a nucleic acid target sequence in TRAC gene.

According to a further embodiment of the invention, the rare-cutting endonuclease is expressed into a cell in order to obtain targeted mutagenesis at the TRAC locus. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the double strand break. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e a mutagenesis event consecutive to an NHEJ event, has occurred can be identified and/or selected by well-known method in the art. As a non-limiting example, deep-sequencing analysis can be generated from the targeted cell genome around the targeted locus. Insertion/deletion events (mutagenesis events) can be therefore detected. As another non-limiting example, assays based on T7 endonuclease that recognizes non-perfectly matched DNA can be used, to quantify from a locus specific PCR on genomic DNA from provided cells, mismatches between reannealed DNA strands coming from cleaved/non-cleaved DNA molecules In a particular embodiment of the methods envisaged herein the mutagenesis is increased by introducing into the cell an additional catalytic domain. In a particular embodiment, the present invention provides improved methods for ensuring targeted modification in the TRAC gene and provides a method for increasing mutagenesis at the target TRAC nucleic acid sequence to generate at least one nucleic acid cleavage and a loss of genetic information around said target nucleic acid sequence thus preventing any scarless re-ligation by NHEJ. In a more preferred embodiment, said catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise at least one protein domain or catalytically active derivative of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a more preferred embodiment, said catalytic domain has an exonuclease activity, in particular a 3'-5' exonuclease activity. In a more preferred embodiment, said catalytic domain is TREX2 or functional variant thereof. In another preferred embodiment, said catalytic domain is encoded by a single chain TREX polypeptide. In a particular embodiment, said catalytic domain is fused to the N-terminus or C-terminus of said rare-cutting endonuclease. It has been found that the coupling of the enzyme TREX2 or single chain TREX2 with an endonuclease such as a meganuclease ensures high frequency of targeted mutagenesis. Alternatively, the above catalytic domain can be separately brought into the cell as part of an independent protein.

Endonucleolytic breaks are known to stimulate homologous recombination. Therefore, in particular embodiments, the present invention also relates to a method for inducing homologous gene targeting in the target nucleic acid sequence further comprising introducing into the cell a donor matrix comprising a sequence homologous to at least a portion of the target TRAC gene, such that homologous recombination occurs between the target nucleic acid sequence and the donor matrix.

In particular embodiments, homologous TRAC gene targeting is achieved by introducing into a cell a rare-cutting endonuclease as described above, to induce a cleavage within or adjacent to a nucleic acid target sequence, as well as a donor matrix comprising a transgene to introduce said transgene by homologous recombination. Following cleavage of the target nucleic acid sequence, a homologous recombination event is stimulated between the genome containing the target nucleic acid sequence and the donor matrix. Said donor matrix comprises a sequence homologous to at least a portion of the target nucleic acid sequence, such that homologous recombination occurs between the target nucleic acid sequence and the donor matrix. Preferably, homologous sequences of at least 50 bp in length, preferably more than 100 bp and more preferably more than 200 bp are used within said donor matrix. Therefore, the donor matrix is preferably from 200 bp to 6000 bp in length, more preferably from 1000 bp to 2000 bp. In another embodiment, said donor matrix comprises two sequences homologous to portions or adjacent portions of said target nucleic acid sequence flanking a sequence to introduce in the target nucleic acid sequence. Indeed, shared DNA homologies are located in regions flanking upstream and downstream the site of the break and the nucleic acid sequence to be introduced should be located between the two homology arms. In particular embodiments, said donor matrix comprises first and second portions which are homologous to region 5' and 3' of the target nucleic acid, respectively. Said donor matrix in these embodiments can also comprise a third portion positioned between the first and the second portion which comprises little or no homology with the regions 5' and 3' of the site of DNA cleavage. In this case, said donor matrix allows introducing new genetic material into a cell. Said new genetic material introduced into a cell can confer a selective or a commercial advantage to said cell. In another embodiment, said donor matrix allows to replace genetic material into a cell. In another embodiment, said donor matrix allows to repair genetic material into a cell.

In particular embodiments, said donor matrix can comprise a positive selection marker between the two homology arms and eventually a negative selection marker upstream of the first homology arm or downstream of the second homology arm. The marker(s) allow(s) the selection of cells having inserted the sequence of interest by homologous recombination at the target site. Depending on the location of the targeted genome sequence wherein cleavage event has occurred, such donor matrix can be used to knock-out a gene, e.g. when the donor matrix is located within the open reading frame of said gene, or to introduce new sequences or genes of interest. Sequence insertions by using such donor matrix can be used to modify a targeted existing gene, by correction or replacement of said gene (allele swap as a non-limiting example), or to up- or down-regulate the expression of the targeted gene (promoter swap as non-limiting example), said targeted gene correction or replacement.

Cells in which a homologous recombination event has occurred can be selected by methods well-known in the art. As a non-limiting example, PCR analysis using one oligonucleotide matching within the exogenous nucleic acid sequence and one oligonucleotide matching the genomic nucleic acid of cells outside said exogenous nucleic acid but close to the targeted locus can be performed. Therefore, cells in which methods of the invention allowed a mutagenesis event or a homologous recombination event to occur can be selected.

The different methods of the invention involve introducing rare-cutting endonuclease or chimeric endonuclease optionally with DNA-end processing enzyme or donor matrix into a cell. As non-limiting example, said rare-cutting endonuclease or chimeric endonuclease optionally with DNA-end processing enzyme or donor matrix can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme. As non-limiting examples, 2A peptide may be used to express into the cell the rare-cutting endonuclease or the chimeric endonuclease and an additional protein domain with a catalytical activity selected from the group consisting of nuclease activity, polymerase activity, kinase activity, phosphatase activity, methylase activity, topoisomerase activity, integrase activity, transposase activity, ligase activity, helicase activity, recombinase activity to process target nucleic acid sequence. The 2A peptide may also be used to express into the cell the rare-cutting endonuclease or the chimeric endonuclease and a fluorescent protein.

Said plasmid vector can contain a selection marker which provides for identification and/or selection of cells which received said vector. Vectors can be introduced into a cell by a variety of methods (e.g., injection, direct uptake, projectile bombardment, liposomes, electroporation). Rare-cutting endonucleases, chimeric endonucleases, DNA-end processing enzyme or donor matrix according to the present invention can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). The polypeptide may be synthesized in situ in the cell as a result of the introduction of polynucleotide encoding polypeptide into the cell. Said protein expression can be induced in selected cells and said rare-cutting endonuclease or chimeric endonuclease cleaves target nucleic acid sequence in selected cells. Alternatively, the polypeptide could be produced outside the cell and then introduced thereto by well-known method of the art.

In another embodiment, said methods of the present invention can be used to generate animals or plants wherein a targeted double-stranded break occurred. Animals may be generated by introducing a rare-cutting endonuclease or a chimeric endonuclease according to the invention into a cell or an embryo. In particular, the present invention relates to a method for generating an animal, comprising providing an eukaryotic cell comprising a nucleic acid target sequence in TCR-alpha gene into which it is desired to introduce a genetic modification; generating a cleavage within or adjacent to the nucleic acid target sequence by introducing an engineered rare-cutting endonuclease or chimeric endonuclease according to the present invention; and generating an animal from the cell or progeny thereof, in which cleavage has occurred. Typically, the embryo is a fertilized one cell stage embryo. Polynucleotides encoding said rare-cutting endonuclease or chimeric endonuclease may be introduced into the cell by any of the methods known in the art including micro injection into the nucleus or cytoplasm of the embryo. In a particular embodiment, the method for generating an animal, further comprise introducing a donor matrix as desired. Said donor matrix comprises a sequence homologous to at least a portion of the nucleic acid target sequence, such that homologous recombination occurs between said donor matrix and the nucleic acid target sequence in the cell or progeny thereof. The donor matrix can include for example a nucleic acid sequence that disrupts a gene after homologous recombination, a nucleic acid sequence that replaces a gene after homologous recombination, a nucleic acid sequence that introduces a mutation into a gene after homologous recombination or a nucleic acid sequence that introduce a regulatory site after homologous recombination. The embryos are then cultured to develop an animal. In one aspect of the invention, an animal in which at least a nucleic acid target sequence of interest has been engineered is provided. For example, an engineered gene may become inactivated such that it is not transcribed or properly translated, or an alternate form of the gene is expressed. The animal may be homozygous or heterozygous for the engineered gene. More particularly, the present invention relates to a method for making an TCR-alpha knock-in or knock-out animal, comprising: a) introducing into a pluripotent precursor cell or embryo of an animal, a rare-cutting endonuclease or chimeric endonuclease as defined above sufficient/capable to induce a nucleic acid cleavage in the nucleic acid target present in TCR-alpha gene; (b) introducing Into the animal precursor cell or embryo of step (a), optionally a donor matrix, wherein said donor matrix comprises a sequence to be introduced flanked by at least one sequence sharing homologies with at least one region of the TCR-alpha gene surrounding the nucleic acid cleavage site of said rare-cutting endonuclease; (c) developing the genomically modified animal precursor cell or embryo of step (b) into a chimeric animal, and (d) deriving a transgenic animal from the chimeric animal of step (c). Preferably, step (c) comprises the introduction of the genomically modified precursors cells generated in step (b) into blastocysts so as to generate chimeric animals.

In another aspect, the present invention relates to an isolated cell comprising a gene encoding the TCR-alpha protein inactivated (e.g., with respect to typical TCR-alpha protein biogenesis and/or TCR-alpha protein cell surface expression and/or with respect to the TCR-alpha protein mediating antigen recognition and immunoreceptor signaling) by the methods described above.

"Cell" or "cells" as used herein refers to any prokaryotic or eukaryotic living cells, cell lines derived from these organisms for in vitro cultures, primary cells from animal origin.

"Primary cell" or "primary cells" as used herein refers to cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

More preferably the animal cell is of the genus i Homo, Rattus, Mus, Sus, Bos, Danio, Canis, Felis, Equus, Salmo, Oncorhynchus, Gallus, Meleagris, Drosophila, Caenorhabditis; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans.*

In aspects of the present invention, the cell can a mammalian cell, a or cell lines derived from these organisms for in vitro cultures or primary cells taken directly from living tissue and established for in vitro culture. As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

In a more preferred embodiment, said isolated cells can be multipotent cells, for example stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. In a particular embodiment of the present invention, the cells are T-cells, preferably human T-cells.

Method for Treating or Preventing Cancer, Autoimmune Disease or Viral Infection

In another aspect, the present invention relates to the use of the I-Onul variants, I-Onul homologue variant or I-Onul derived chimeric endonuclease according to the invention as a medicament.

More particularly, the present invention relates to a method for treating a subject having cancer, autoimmune disease or viral infection comprising of introducing into a cell a rare-cutting endonuclease or chimeric endonuclease according to the invention sufficient to provide for mutagenesis or homologous recombination in the TRAC gene, optionally with a donor matrix and/or DNA-end processing enzyme and administrating the cells to the subject. In particular aspects, the method can combine the introduction of a rare-cutting endonuclease or chimeric endonuclease with the introduction of an artificial/chimeric antigen receptor recognizing a tumor, virus or autoimmune-related target. In certain embodiment, the method can comprise selecting cultured cells in which the mutagenesis or homologous recombination event has occurred in the TRAC gene by well-known methods in the art.

Said treatment can be ameliorating, curative or prophylactic. It may be either part of an autologous or part of an allogenic treatment. By autologous, it is meant that cells, cell line or population of cells used for treating patients are originating from said patient. By allogeneic is meant that the cells or population of cells used for treating patients are not originating from said patient but from a donor.

Cells that can be used with the disclosed methods can be multipotent cells, for example stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells or human T-cells. Prior to expansion and genetic modification of the cells of the invention, a source of cells can be obtained from a subject through a variety of non-limiting methods. T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used.

In another embodiment, isolated cells obtained by the different methods or cell line(s) derived from said isolated cells can be used as a medicament. In another embodiment, said medicament can be used for treating cancer or autoimmune disease or viral infection in a patient in need thereof. In another embodiment, said isolated cell according to the invention or cell line derived from said isolated cell can be used in the manufacture of a medicament for treatment of a cancer, autoimmune disease or viral infection in a patient in need thereof.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

In particular aspects, the administration of the cells or population of cells comprises the administration of $10^4$ to $10^9$ cells/kg body weight, preferably $10^5$ to $10^6$ cells/kg body weight, including all values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a cell bank or a donor. While individual needs vary, determination of optimal ranges of effective amounts of a given cell type for a particular disease or conditions within the skill of the art. The dosage administrated will be dependent upon the age, health and weight of the recipient, kind of concurrent treatment, if any, frequency of treatment and the nature of the effect desired.

In another embodiment, the administration of cells may be combined with administration of an immunosuppressive drug regimen. The immunosuppressive regiment may include, but not limited to, cytostatic, glucocorticoids and antibody-based drug classes. The immunosuppressive regimen may be administered before, during or after administration of cells. The immunosuppressive regimen can be administered in one or more doses. The dosage, timing and composition of the immunosuppressive drug regimen are within the judgment of managing physician and depend on the clinical condition of the patient.

In another embodiment, the present invention relates to a method for targeting TCR-alpha gene in a subject, the method comprising administrating to a subject a vector encoding a rare-cutting endonuclease according to the present invention.

Definitions

In the description above, a number of terms are used extensively. The following definitions are provided to facilitate understanding of the present embodiments.

As used herein, the term "about" indicates that a value includes the inherent variation of error for the method being employed to determine a value, or the variation that exists among experiments.

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or C.

As used herein, "nucleic acid" or "nucleic acid molecule" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "chimeric endonuclease" it is intended to mean an endonuclease which comprise functional portions of an endonuclease operationally linked to one or more protein functional domains coming from another protein.

The terms "fusion protein" or "chimeric protein" indicate that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a host cell as a single protein. A fusion protein can comprise at least part of one polypeptide fused with another polypeptide. In some embodiments, a fusion protein can comprise at least a part of one polypeptide fused with at least a part of the same polypeptide.

by "screening" it is intended to mean the sequential or simultaneous selection of one or more meganuclease variant(s) which exhibits a specified phenotype such as altered cleavage activity.

by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "transgene" refers to a sequence encoding a polypeptide. Preferably, the polypeptide encoded by the transgene is either not expressed or expressed but not biologically active, in the cell, tissue or individual in which the transgene is inserted. Most preferably, the transgene encodes a therapeutic polypeptide useful for the treatment of an individual.

By "delivery vector" or "delivery vectors" is intended any delivery vector which can be used in the present invention to put into cell contact (i.e "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

by "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

by "integrative lentiviral vectors (or LV)", is meant such vectors as non limiting example, that are able to integrate the genome of a target cell.

At the opposite by "non integrative lentiviral vectors" (or NILV) is meant efficient gene delivery vectors that do not integrate the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Delivery vectors and vectors can be associated or combined with any cellular permeabilization techniques such as sonoporation or electroporation or derivatives of these techniques.

The term "endonuclease", or "nuclease" refers to any wild-type or variant enzyme capable of catalyzing the hydrolysis (cleavage) of bonds between nucleic acids within a DNA or RNA molecule, preferably a DNA molecule. Endonucleases can be classified as rare-cutting endonucleases when having typically a polynucleotide recognition greater than 12 base pairs (bp) in length, more preferably of 14-45 bp. Rare-cutting endonucleases significantly increase HR by inducing DNA double-strand breaks (DSBs) at a defined locus (Perrin, Buckle et al. 1993; Rouet, Smih et al. 1994; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) (Eisenschmidt, Lanio et al. 2005; Arimondo, Thomas et al. 2006; Simon, Cannata et al. 2008), A TALE-nuclease or a chemical endonuclease. In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Transcription Activator Like Effector (TALE) is a family of proteins used in the infection process by plant pathogens of the *Xanthomonas* genus (Boch, Scholze et al. 2009; Moscou and Bogdanove 2009; Christian, Cermak et al. 2010; Li, Huang et al. 2011; Li, Huang et al. 2011). The term "TAL effector nuclease" (TALE-Nuclease) refers to a nuclease comprising a TAL-effector domain fused to a nuclease domain. These DNA binding domains may be engineered to bind to a desired target and fused to a nuclease domain, such as the Fok1 nuclease domain, to derive a TAL effector domain-nuclease fusion protein.

The term "Zinc-finger nuclease" (ZFN) refers to artificial restriction enzymes generated by fusing a zinc finger DNA-binding domain to a DNA-cleavage domain. Zinc finger domains can be engineered to bind to a desired target site. In some embodiments, the cleavage domain comprises the non-specific cleavage domain of FokI (Porteus and Carroll 2005). In other embodiments, the cleavage domain comprises all or an active portion of another nuclease.

By "catalytic domain" is intended the protein domain or module of an enzyme containing the active site of said enzyme; by active site is intended the part of said enzyme at which catalysis of the substrate occurs. Enzymes, but also their catalytic domains, are classified and named according to the reaction they catalyze. The Enzyme Commission number (EC number) is a numerical classification scheme for enzymes, based on the chemical reactions they catalyze.

The term "exonuclease" refers to enzymes that cleave phosphodiester bonds at the end of a polynucleotide chain via a hydrolyzing reaction that breaks phosphodiester bonds at either the 3' or 5' end. The polynucleotide may be double-stranded DNA (dsDNA), single-stranded DNA (ssDNA), RNA, double-stranded hybrids of DNA and RNA, and synthetic DNA (for example, containing bases other than A, C, G, and T). The term "5' exonuclease" refers to exonucleases that cleave the phosphodiester bond at the 5' end. The term "3' exonuclease" refers to exonucleases that cleave the phosphodiester bond at the 3' end. Exonucleases may cleave the phosphodiester bonds at the end of a polynucleotide chain at endonuclease cut sites or at ends generated by other chemical or mechanical means, such as shearing, ionizing radiation, ultraviolet radiation, oxygen radicals, chemical hydrolosis and chemotherapy agents. Exonucleases may cleave the phosphodiester bonds at blunt ends or sticky ends. *E. coli* exonuclease I and exonuclease III are two commonly used 3'-exonucleases that have 3'-exonucleolytic single-strand degradation activity. Other examples of 3'-exonucleases include Nucleoside diphosphate kinases (NDKs), NDK1 (NM23-H1), NDK5, NDK7, and NDK8, WRN, and Three prime repair exonuclease 2 (Trex2). *E. coli* exonuclease VII and T7-exonuclease Gene 6 are two commonly used 5'-3' exonucleases that have 5% exonucleolytic single-strand degradation activity. The exonuclease can be originated from prokaryotes, such as *E. coli* exonucleases, or eukaryotes, such as yeast, worm, murine, or human exonucleases.

by "functional mutant" is intended a catalytically active mutant of a protein or a protein domain; such mutant can have the same activity compared to its parent protein or protein domain or additional properties. This definition applies to chimeric proteins or protein domains that constitute chimeric proteins according to the present invention. Are also encompassed in the scope of this definition "derivatives" of these proteins or protein domains that comprise the entirety or part of these proteins or protein domains fused to other protein or chemical parts such as tags, antibodies, polyethylene glycol as non-limiting examples.

By nucleic acid or protein "homologous sequence" it is meant a sequence with high percentage of identity or high percentage of homology with sequences at nucleotidic or polypeptidic levels. By high percentage of identity or high percentage of homology it is intended at least 70%, more preferably at least 75%, more preferably at least 80%, more preferably at least 85%, more preferably at least 90%, more preferably at least 95%, more preferably at least 97%, more preferably at least 99% or any percentage value between 70% and 99%.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

The terms "target site", "target sequence", "target nucleic acid sequence" or "nucleic acid target sequence" refer to a nucleic acid sequence that defines a portion of a nucleic acid to which a binding molecule will bind and/or cleave, provided sufficient conditions for binding and/or cleaving are present.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., an endonuclease domain, a polynucleotide binding domain, such as a DNA-binding domain, or an end-processing domain).

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity.

Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity.

The term "subject" as used herein includes all members of the animal kingdom including non-human primates and humans.

EXAMPLES

Example 1: Engineering of LHE Prototypes with DNA Recognition Interfaces Specific for Targets in the Human TRAC Gene was Performed Putative LHE target sequences in the human TRAC gene were first identified for which high quality engineered DNA recognition interfaces were predicted by the inventor. Such predictions are based on a series of features intrinsic to the LHE scaffold, I-Onul (SEQ ID NO: 1), upon which the TRAC DNA recognition interfaces were to be engineered. Other considerations, such as locations within the TRAC gene likely to cause significant disruptions to the TCR-alpha protein upon endonuclease-mediated insertions or deletions, and/or the occurrence of adjacent downstream TGA, TAG, or TAA stop codons in alternative reading frames to limit the production of out-of-frame peptides which could serve as the basis for immunological rejection, were also incorporated into the target choice process. See FIG. 1 which schematically illustrates the locations of the putative target sequences.

Figure 2:
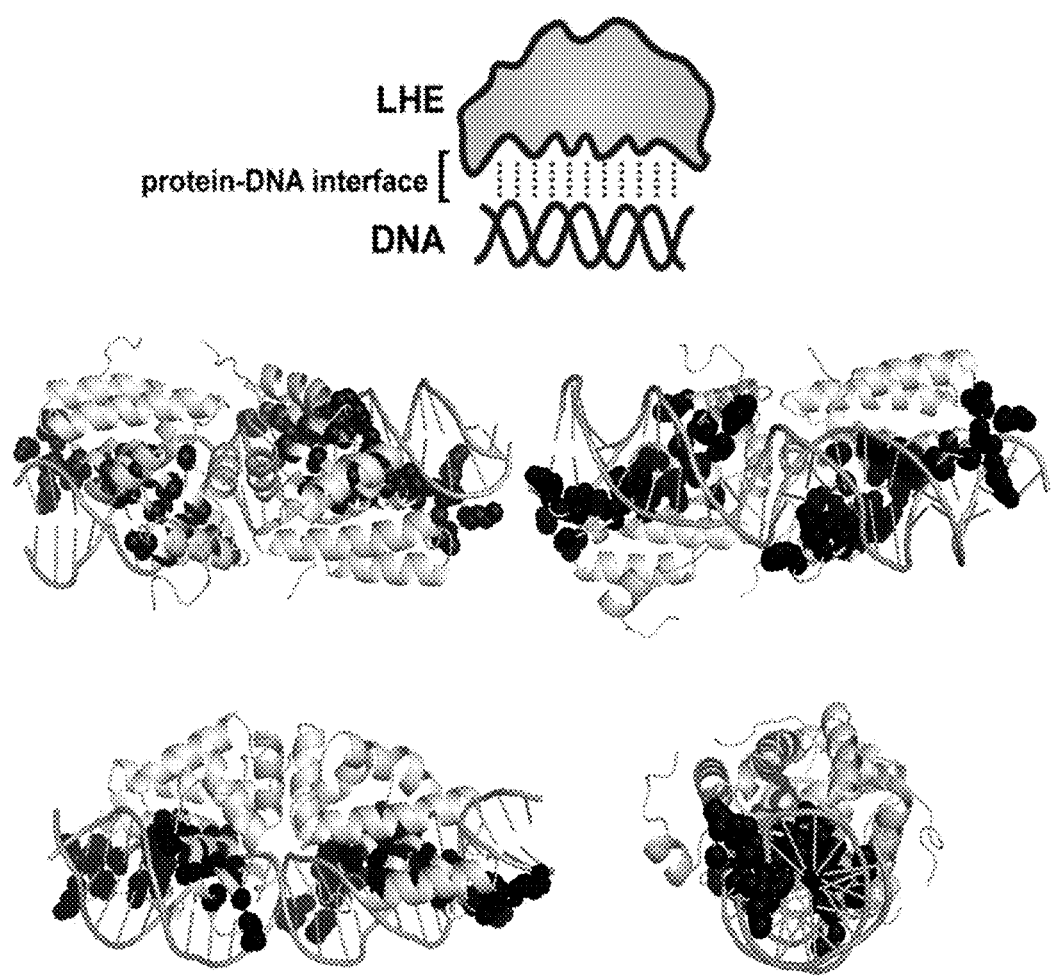
FIG. 2 shows schematically and structurally the location of the protein-DNA interface that defines the interaction between a LAGLIDADG homing endonuclease (LHE) and its DNA substrate. The schematic illustration generally depicts the concept that there is a continuous region of the LHE that comprises the interaction with DNA. The structural images demonstrate in more detail the nature of this interaction, whereby the protein-DNA interfacial residues of the LHE (whose side-chain atoms are shown as black spheres) interdigitate into the major grooves of DNA helix. It is the constellation of interfacial side chain atoms which determine the complementarity of a natural or engineered LHE to the atoms of the DNA nucleotides, which themselves form sequence specific patterns.
Figure 3:
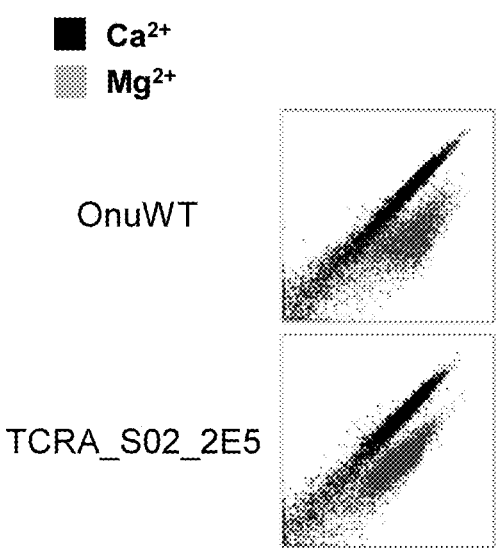
FIG. 3 shows that, of the two target sites that were chosen for protein-DNA interface engineering, only one (TCRA_S02) yielded variant LHEs capable of cleaving the full target sequence. One of these variants is shown in comparison with I-Onul enzyme and its cognate target. The panels depict flow cytometric analysis of DNA hydrolysis, whereby the baker's yeast, *Saccharomyces cerevisiae*, express the LHE on the surface of their cells and are interrogated with fluorescent dye-labelled synthetic DNA substrates as has been published. Briefly, samples are first stained with a biotinylated antibody to an epitope appended to the N- or C-terminus of the LHE. During this staining procedure, conjugates of phycoerythrin-labeled streptavidin (x-axis) with biotin- and Alexa fluor-647 (y-axis) labeled synthetic DNA substrates are generated at a relative molarity that preserves some biotin binding sites on the streptavidin. These pre-conjugates are then used to counter stain the yeast cells, resulting in the co-linear streptavidin-PE/Alexa fluor-647 profile. Cleavage-inhibiting (Ca2+) and cleavage-permitting (Mg2+) conditions are then used to determine whether the native or engineered LHE cleaves the tethered target, which, if cleaved, loses signal in the y-axis owing to loss of the Alexa fluor-647 fluorophore.

Two putative target sequences (TCRA_S02 and TCRA_S10; SEQ ID NO: 3 and SEQ ID NO: 4) were chosen for the initial stages of engineering the DNA recognition interface. Variant libraries were constructed whereby amino acid residues in localized sub-regions of the DNA recognition interface were varied. See FIG. 2 which shows schematic and structural diagrams of the DNA recognition interface. Variation within the DNA recognition interface of I-Onul nucleic acid sequence (SEQ ID NO: 1) was achieved by incorporating degenerate codons into oligonucleotides which served as substrates for PCR reactions to generate variant libraries by gap recombination in the yeast strain *Saccharomyces cerevisiae*. The resulting libraries were screened for target cleavage activity by surface display and flow cytometry based methods as has been described in (Jarjour, West-Foyle et al. 2009). In this manner, the specificity of the DNA recognition interface was altered to recognize targets in the human TRAC gene. In particular aspects, successfully re-specified DNA recognition interfaces were achieved for TCRA_S02 (SEQ ID NO: 3) only, with the process failing for the other putative target site at earlier stage in the engineering process. See FIG. 3 illustrating the successful isolation of variants cleaving the TCRA_S02 target.

Example 2: LHEs with Engineered DNA Recognition Interfaces were Shown to Cause Disruptive Mutations to the Target Sequences for which they were Engineered to Recognize To measure the activity of the TCRA targeting LHE, a chromosomally integrated fluorescent reporter system that has been described previously was used. In this system, the LHE of interest is transfected into a HEK 293T fibroblast cell line that is engineered to contain the TCRA_S02 target sequence upstream of an out-of-frame gene encoding the fluorescent protein mCherry. Cleavage of the embedded TCRA_S02 target and subsequent small insertions or deletions caused by DNA repair via the non-homologous end joining (NHEJ) pathway result in approximately 1 out of three repaired loci placing the fluorescent reporter gene 'in-frame'. Fluorescence in the mCherry channel on a flow cytometer is therefore a surrogate high-throughput readout of LHE cleavage of the chromosomally embedded TCRA_S02 target sequence.

Figure 4:
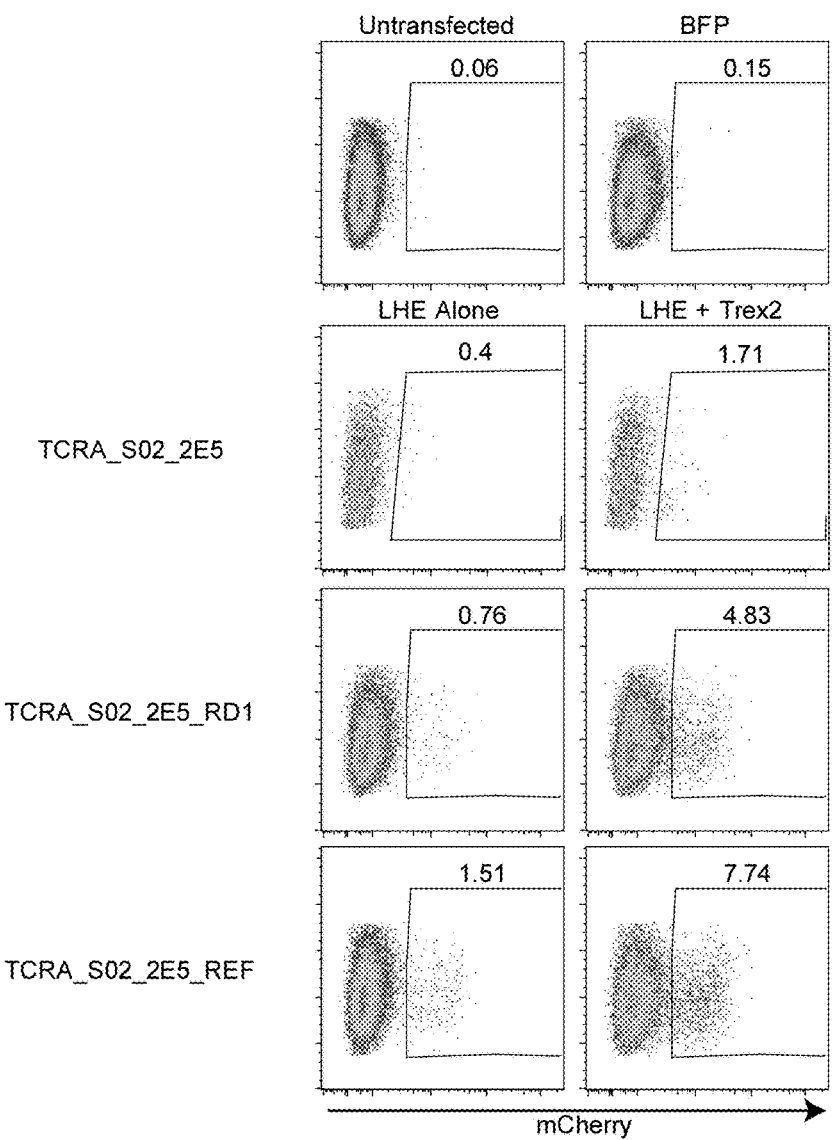
FIG. 4 shows the initial targeting efficiency of the TCRA_S02_2E5 variant and the progressive improvements in the targeting efficiency achieved by the activity refinement process. Targeting efficiency was measured using a chromosomally integrated double-strand break fluorescent reporter termed the 'traffic light reporter' (TLR). Human embryonic kidney 293T (HEK 293T) fibroblasts were constructed to contain the TCRA_S02 DNA sequence immediately upstream of an out-of-frame mCherry fluorescent protein (y-axis) which, upon one of three possible frame outcomes of the NHEJ DNA repair process becomes fluorescent. The percentage of cells in the y-axis therefore represents approximately ⅓ of all imprecise nuclease-mediated repair events. This cell line was then transfected with synthetically generated in vitro transcribed mRNA (IVT-mRNA) encoding the TCRA_S02 targeting LHEs, with or without mRNA encoding for Trex2 exonuclease. The original TCRA_S02_2E5 variant inefficiently caused double-stranded breaks and therefore produced only small percentages of mCherry positive cells ($2^{nd}$ row). Two rounds of activity refinement screening led to vast improvements in the generation of mCherry positive cells.

Initial results with the TCRA_S02_2E5 variant (SEQ ID NO: 5 encoding SEQ ID NO: 6) showed very low efficiency of mCherry expression, indicating that this variant was not very actively cleaving its target in a cellular chromosomal context. Random mutagenesis of the TCRA_S02_2E5 variant and surface display-based screening under more stringent cleavage conditions to isolate variants with improved catalytic activities were performed. Two rounds of mutagenesis and screening led to variants with 40- to 50-fold higher rates of generating mCherry expressing cells. See FIG. 4 illustrating the flow cytometry read-outs from the reporter assay for TCRA_S02_2E5 refined variants, which included TCRA_S02_2E5_RD1_08 (SEQ ID NO: 7 encoding SEQ ID NO: 8) and TCRA_S02_2E5_RD2_23 (SEQ ID NO: 9 encoding SEQ ID NO: 10). A top performing variant TCRA_S02_2E5_RD1_08 (SEQ ID NO:7) contained six mutations relative to the TCRA_S02_2E5 variant, four of which are located within the DNA recognition interface and two are located elsewhere in the LHE. See FIG. 5 and FIG. 16 which provide the relative alignments of the indicated variants as well as the positional information of the residues comprising the DNA recognition interface. It is unknown to what extent, if any, the individual mutations identified through this process contribute to the characteristics of the LHE which influence its DNA recognition and cleavage activity. Taken together they led to significant improvements in the frequency of the occurrence disruptive mutations to the TCRA_S02 target sequence.

Figure 6:
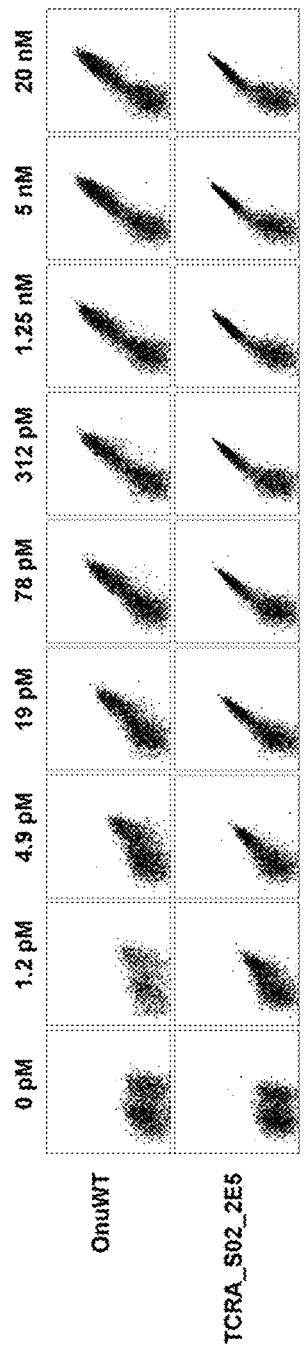
FIG. 6 shows an assay whereby DNA binding titration is used to establish the affinity properties of two different LHEs targeting the TCRA_S02 site. Samples of yeast displaying each LHE variant were independently incubated with increasing concentrations of fluorescent dye-labeled synthetic DNA substrates (y-axis). An antibody to a C-terminal epitope was also included (x-axis) such that DNA binding activity could be normalized to the amount of LHE protein expressed on the yeast surface, creating the co-linear pattern, with higher signal in the y-axis per x-axis signal where affinity is greater. The results demonstrate that the I-Onul LHE (OnuWT) has an approximate Kd of approximately 80 pM and the TCRA_S02_2E5 variant has a Kd of approximately 90 pM.
Figure 7:
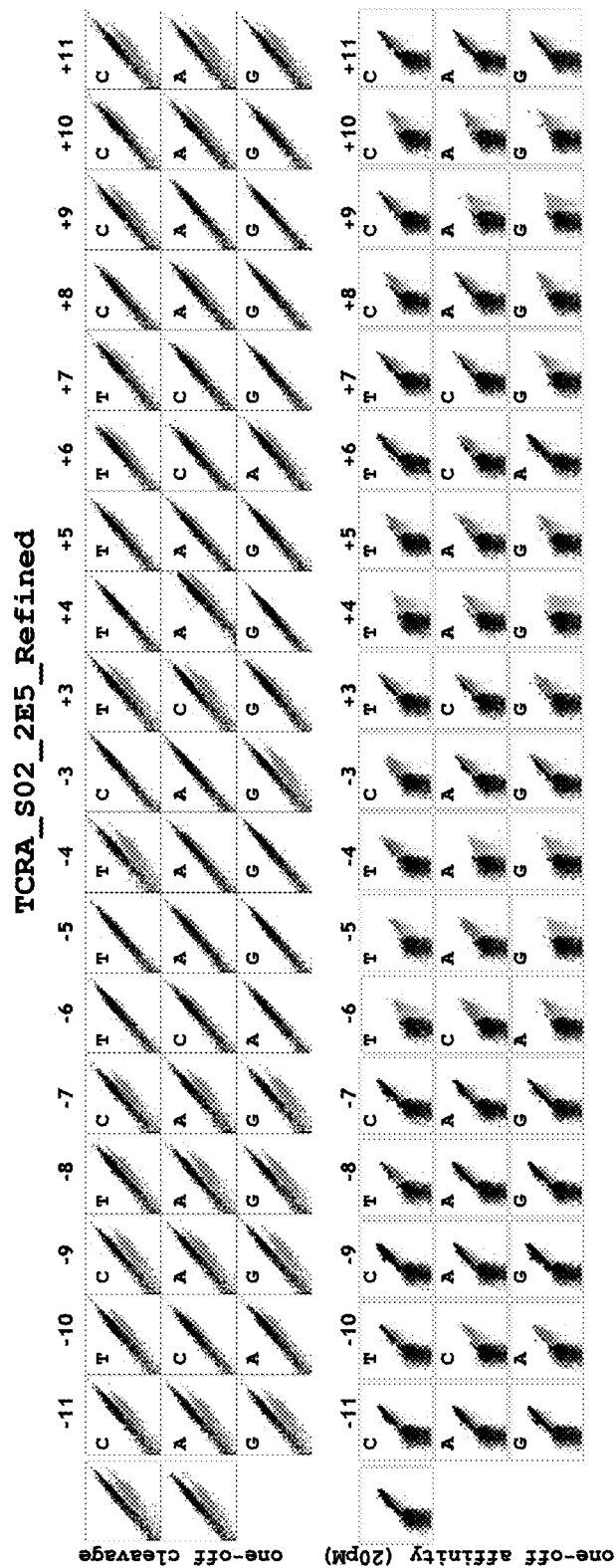
FIG. 7 shows the specificity profiling of the TCRA_S02_2E5_RD2_8 LHE variant using cleavage (top panels) and affinity (bottom panels) analysis. Cleavage and affinity analysis was performed as described in FIGS. 3 and 4 respectively, however panels of DNA substrates were tested whereby each of the 22 positions along the target was serially altered to each of the 3 non-native base pairs and tested in cleavage-inhibiting and cleavage-permitting conditions. The resulting cleavage and affinity profiles for the 67 different substrates (the target in the TRAC gene and the 66 'one-off' substrates) indicate which LHE variants have most ideal specificity properties and are therefore better candidates for applications demanding tighter specificity, such as in human therapeutics.

Example 3: LHEs with DNA Recognition Interfaces Having High Affinity, High Specificity, and Low Toxicity were Differentiated The LHE containing the engineered DNA recognition interfaces for the TCRA_S02 (SEQ ID NO: 3) target was tested for affinity, specificity, and toxicity characteristics. Affinity was tested by independently incubating yeast displaying the TCRA_S02_2E5_RD1_08 variant, (SEQ ID NO: 7, encoding SEQ ID NO: 8) with DNA substrates containing its target sequences at various concentrations. See FIG. 6 showing the affinity properties of this variant relative to the wild-type I-Onul protein. These data demonstrate that the TCRA_S02_2E5_RD1_08 variant binds its DNA target with affinities comparable or higher than that of the interaction between the native I-Onul LHE and its target sequence (SEQ ID NO: 11). Specificity was tested by analyzing the relative affinity and DNA-cleaving ability of the LHE variant towards target sequence containing each of the three alternate DNA base pairs at each position along the substrate. See FIG. 7 illustrating the specificity profile of the TCRA_S02_2E5_RD1_08 (SEQ ID NO: 7) variant. These data demonstrate that the TCRA_S02_2E5_RD1_08 LHE variant has a high overall specificity, as it exclusively cleaves/binds to its specific substrate base pair in most positions along its target, not tolerating substitutions. Toxicity was analyzed by in vitro transcribing each LHE into mRNA and transfecting primary human T cells by electroporation, followed by flow cytometry analysis of the survival of the cells relative to transfection with a control mRNA encoding a blue fluorescent protein (BFP). See FIG. 8 showing flow cytometry analysis of primary human T cells after electroporation with IVT-mRNA coding for TCRA_S02_2E5 RD1_08 LHE variant. These data show that the TCRA_S02 LHE variants have minimal toxicity in primary human cells.

Figure 9:
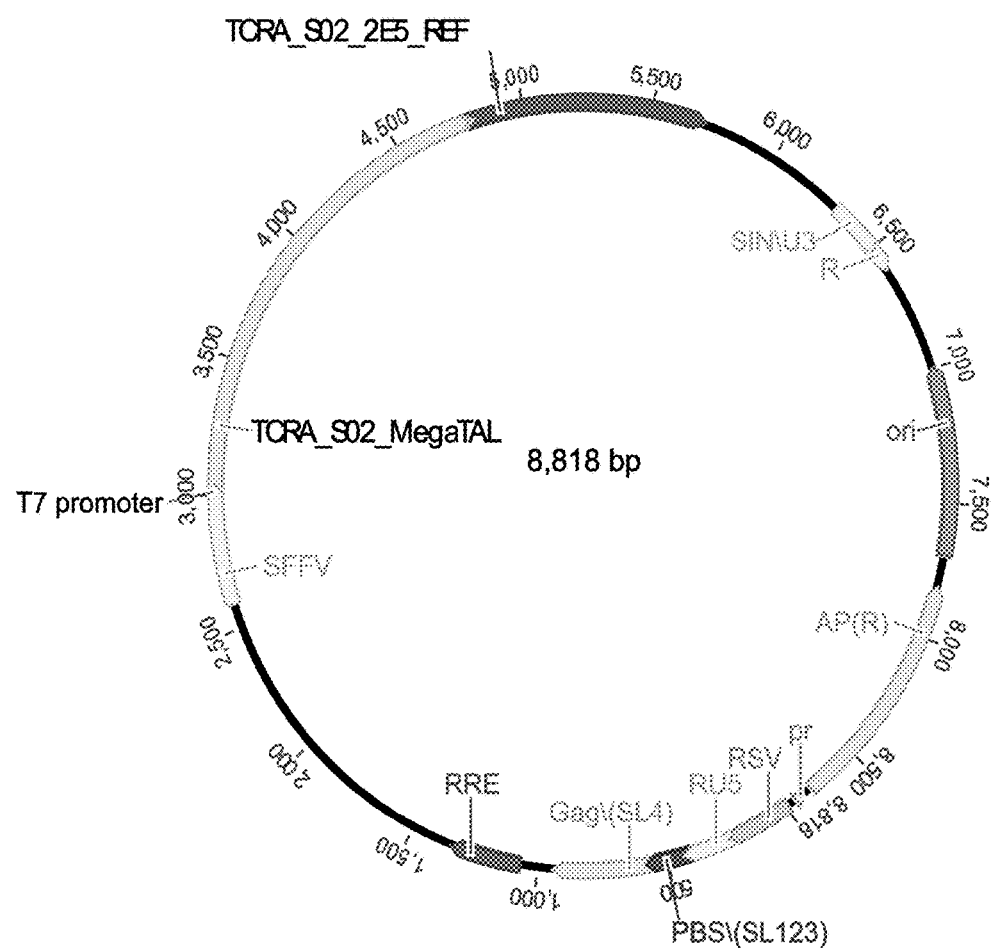
FIG. 9 shows a schematic of a self-inactivating (SIN) lentiviral production plasmid from which lentivirus preparations were generated and used as vectors for the transduction of cell lines and primary cells (A) (SEQ ID NO: 12 and SEQ ID NO: 13) as well as an exemplary non-limiting vector containing the MegaTAL construct used either in lentiviral production or for in vitro transcription for the production of IVT-mRNA (B) (SEQ ID NO: 12). The primary features of the vector, in addition to the lentiviral features well known to those familiar with the art such as the long terminal repeats (LTRs), primer binding site (PBS), central polypurine tract (cPPT), and a T7 RNA promoter (T7) are multicistronic elements for the expression of a TCRA-targeting LHE (as shown) or MegaTAL linked via a T2A peptide linker motif to the Trex2 exonuclease which further carries an internal ribosomal entry site (IRES) and blue fluorescent protein (BFP) for tracking transduced cells.

Example 4: Transient Expression of TRAC-Targeting LHE was Shown to Cause Loss of TCR-Alpha Protein from the Cell Surface and Lead to Disruptive Mutations at the TRAC Gene Next, the TRAC-targeting LHE was examined to determine whether: i) it efficiently cleaved the TCRA_S02 target site in the TRAC gene in human cells (SEQ ID NO: 3); and ii) the resulting NHEJ-mediated disruptions resulted in the loss of the TRAC protein from the cell surface. One primary motivation for achieving high efficiencies is in developing human therapeutic interventions based on TRAC disrupting nucleases. In such an application, using viral vectors which permanently (such as for retroviral, lentiviral, or foamy viral vectors) or transiently (such as adenoviral or adeno-associated viral vectors) deliver nuclease reagents is laborious, cost and resource-intensive, poorly scalable, and challenging to address from a regulatory perspective. A more attractive therapeutic reagent and process would involve replacing the biological vector with a synthetic expression reagent, such as in vitro transcribed mRNA (IVT-mRNA). Primary human T cells were transfected with in-vitro transcribed mRNA (IVT-mRNA) encoding either BFP or the TCRA_S02_2E5 LHE, or variants as described above using methods well known to those familiar with the art. Electroporation of IVT-mRNA produce a transient burst of protein expression lasting 4 to 12 hours. The duration and extent of protein expression depends on the structure of IVT-mRNA. An example of the plasmid used for IVT-mRNA production is shown in FIG. 9 (SEQ ID NO: 12). The secondary mRNA stability factors are added in the course of IVT-mRNA production. The 5' mRNA cap (m7G) regulates expression by binding to eukaryotic initiation factors (eIF). Addition of a polyadenylated (poly(A)) tail delays IVT-mRNA degradation and increase IVT-mRNA protein expression.

Figure 10:
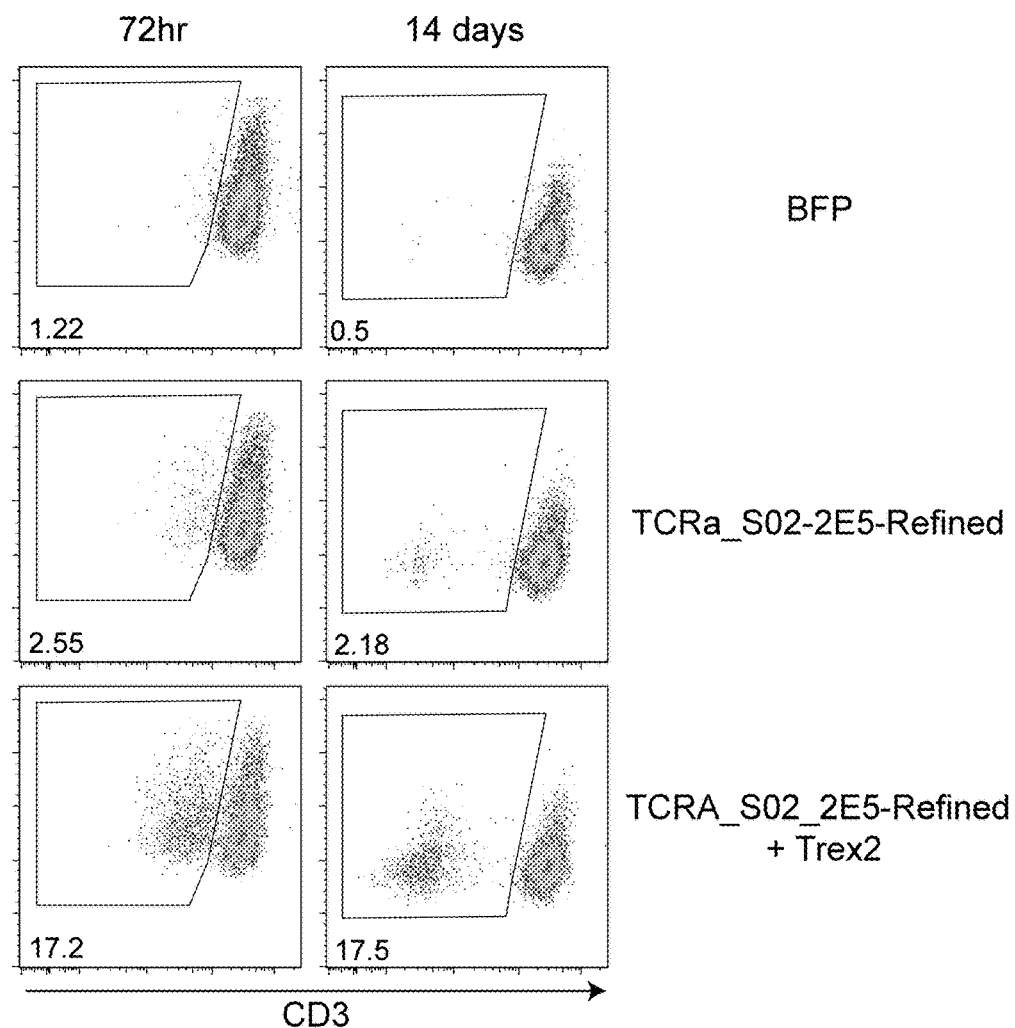
FIG. 10 shows the complete loss of expression of the TCR-alpha protein from the cell surface of primary human T cells transfected with IVT-mRNA encoding for TCRA_S02_RD2_8 LHE variant in conjunction with IVT-mRNA encoding for accessory Trex2 exonuclease protein. The flow cytometry panels represent different time-point analysis following mRNA transfection (left panel: 72 hr, right panel: 14 days). The presence of TCR-alpha protein on the cellular surface is detected via an antibody specific for the CD3 co-receptor molecule. Surface expression of the CD3 co-receptor requires functional expression of the TCR-alpha protein and the absence of a CD3 signal signifies successful disruption of the TRAC gene.
Figure 11:
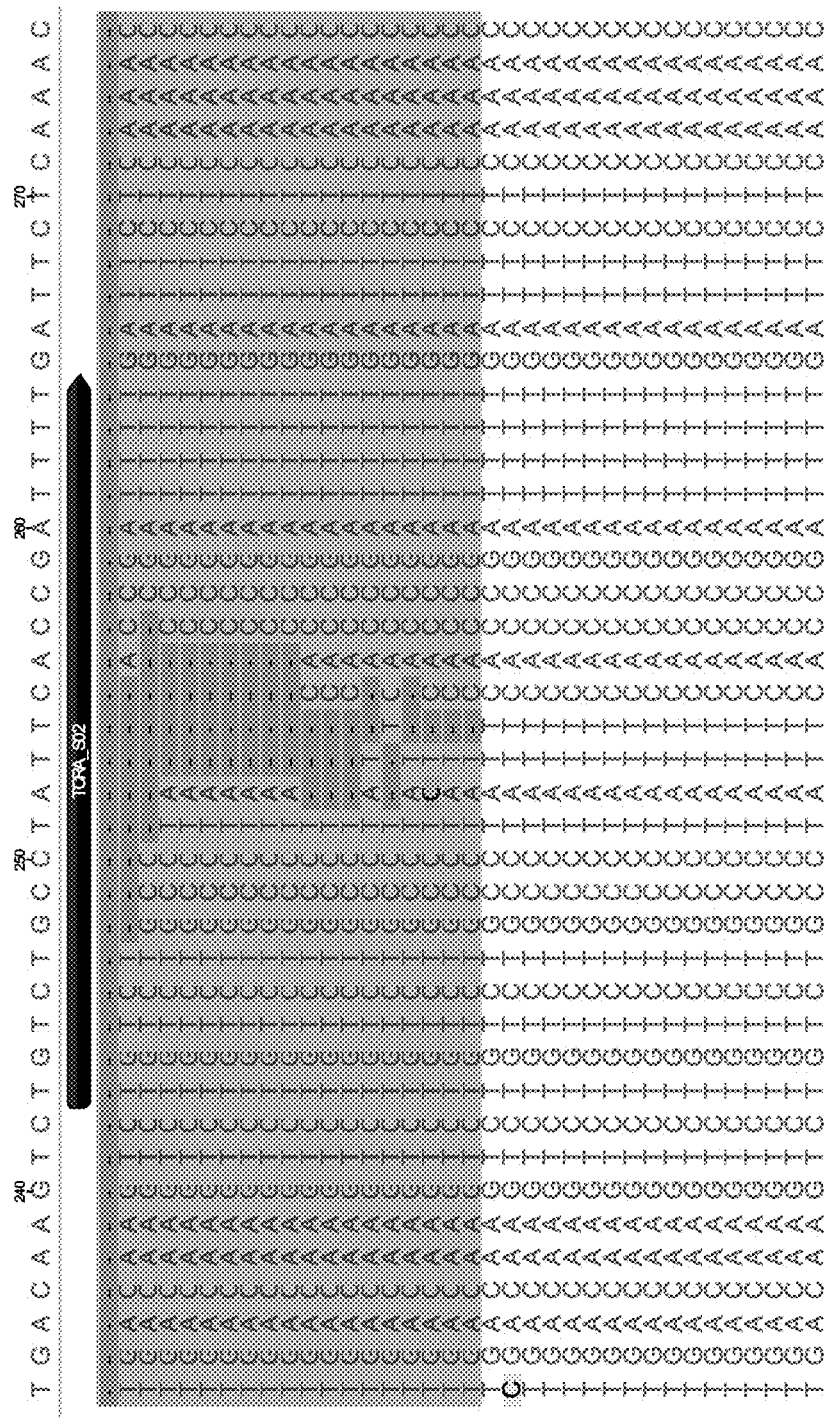
FIG. 11 shows gene sequencing data (SEQ ID NOs:19-54) at the TCRA_S02 target site from cells treated with TCRA_S02_RD2_8 LHE variant. Primary T cells transfected with IVT-mRNA encoding for TCRA_S02_RD2_8 LHE variant in conjunction with IVT-mRNA encoding for Trex2 exonuclease were cultured and purified using flow cytometric selection of CD3-negative cells. The sorted CD3-negative cells have deletions at 50% of the TCRA alleles, consistent with the non-silenced TRAC allele being the primary target for TCRA_S02 LHE variants.

Three day after electroporation of primary human T cells with IVT-mRNA encoding TRAC-targeting LHE and Trex2, greater than 15% of cells had lost cell surface expression of the TCR-alpha protein. See FIG. 10 demonstrating the flow cytometric analysis of TRAC disruption and stability of TRAC disruption over a two week culture period. The TCR-alpha-negative cells were sorted using flow cytometry and the TCRA_S02 target site on the TRAC gene was sequenced to analyze the genetic disruption of TRAC gene and to confirm and characterize the spectrum of LHE-induced mutations. The TRAC gene is expressed in a mono-allelic fashion, due to silencing of the non-productive allele during T cell development. See FIG. 11 for sequencing results showing that 50% of all TRAC alleles contained NHEJ disruption events at TCR_S02 target site. The critical conclusion is that the TCRA_S02_LHE variants effectively target the actively transcribed TRAC allele to block TCR-alpha expression.

Figure 12:
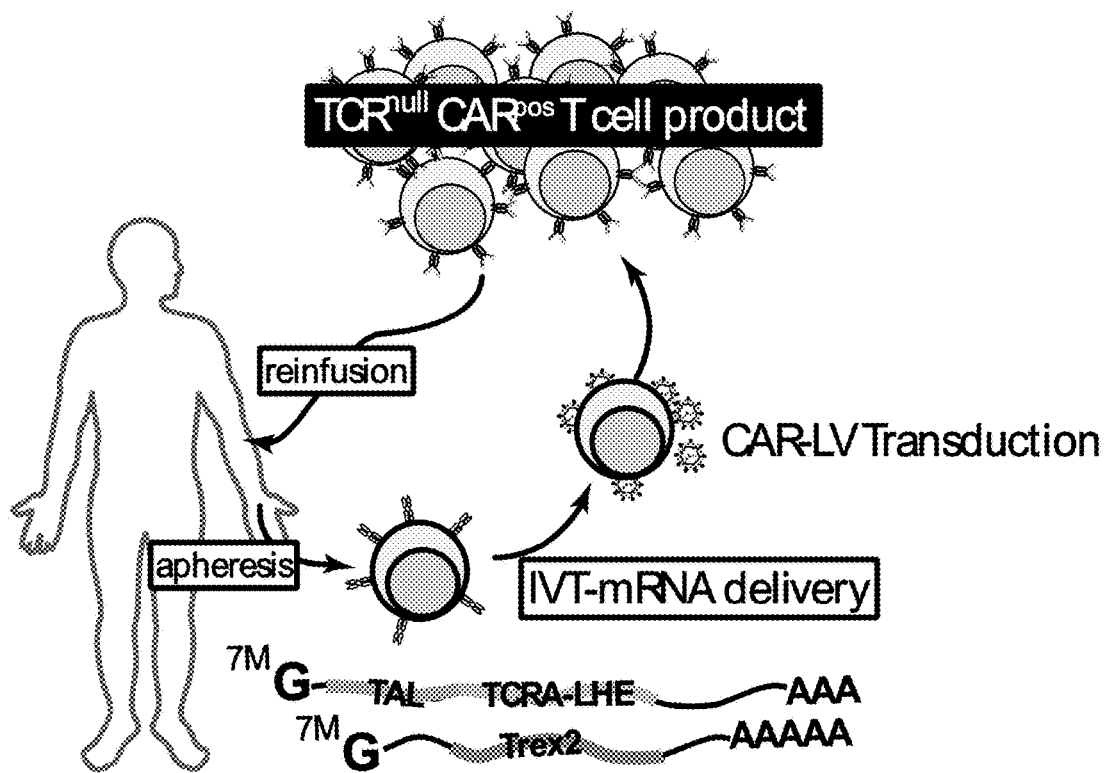
FIG. 12 depicts schematically one treatment strategy that could be used to generate populations of TCRA-deficient T cells for the treatment of cancer, autoimmunity or chronic viral infection. Briefly, peripheral blood mononuclear cells (PBMCs) would be isolated by apheresis, processed to purify and culture T cells, treated with TRAC-targeting nuclease delivery agents, combined with artificial antigen receptors (CARs) and reinfused into the patient.

Example 5: TRAC-Targeting LHE was Improved by Fusion with TALE Domains, Enabling More Efficient TRAC Gene Disruption with Transient Synthetic Delivery Methods The results of the examples provided above demonstrate that the nuclease reagents described herein are able to effectively generate primary cells lacking TCR-alpha expression. The key goal of the LHE enzyme and variants described wherein is generation of TCR-alpha deficient T cells for the treatment of cancer, autoimmunity and viral infection. See FIG. 12 which schematically illustrates the proposed therapeutic strategy by which TRAC-targeting LHE is combined with a secondary CAR reagent to produce T cells for the treatment of cancer and other diseases. Our initial studies with TCRA_S02 targeting LHE and Trex2 delivery in the IVT-mRNA form showed promising but suboptimal overall rates of TRAC gene disruption. While not limiting, higher rates of TCR-alpha disruption would simplify product manufacturing and result in reduced development costs.

Figure 13:
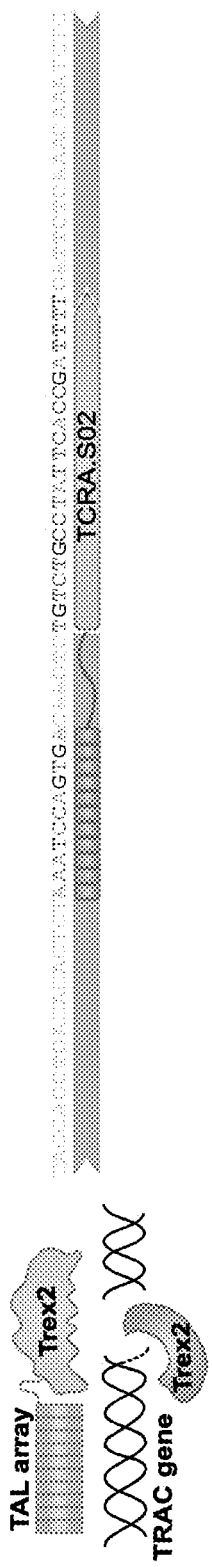
FIG. 13 shows a schematic representation of the ultra-efficient TRAC gene disruption technology based on the combination of the MegaTAL architecture and Trex2 expression. Also shown is the TCRA_S02 MegaTAL target sequence (SEQ ID NO: 55) within the DNA of the TRAC gene, with the location of the 11-mer TALE array indicated both schematically (repetitive units are not annotated but shown upstream of the TCRA_S02 annotation) and its sequence is shown in bold.
Figure 14:
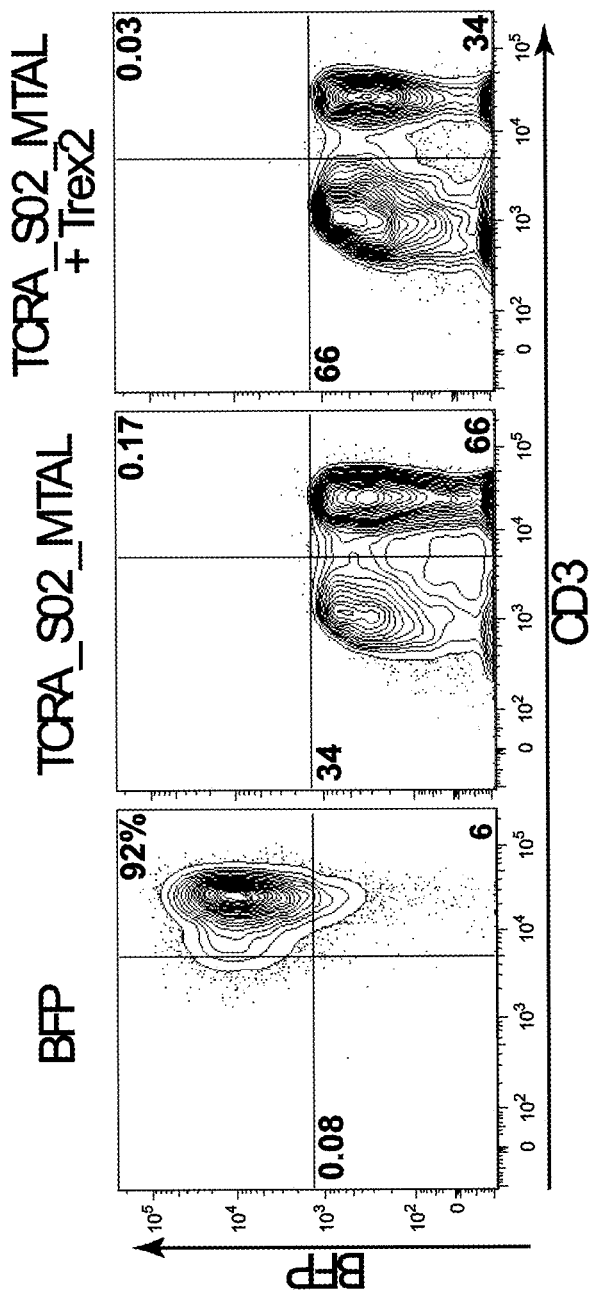
FIG. 14 demonstrates the extremely high efficiency of TCR-alpha protein removal from the cell surface of primary human T cells transfected with IVT-mRNA encoding for TCRA_S02_MegaTAL LHE variant in conjunction with IVT-mRNA encoding for accessory Trex2 exonuclease protein. The flow cytometry panels demonstrate the TCR complex assembly following electroporation with a fluorescent protein control (BFP) or TCRA_S02 MegaTAL LHE variant with or without IVT-mRNA encoding for Trex2.
Figure 15:
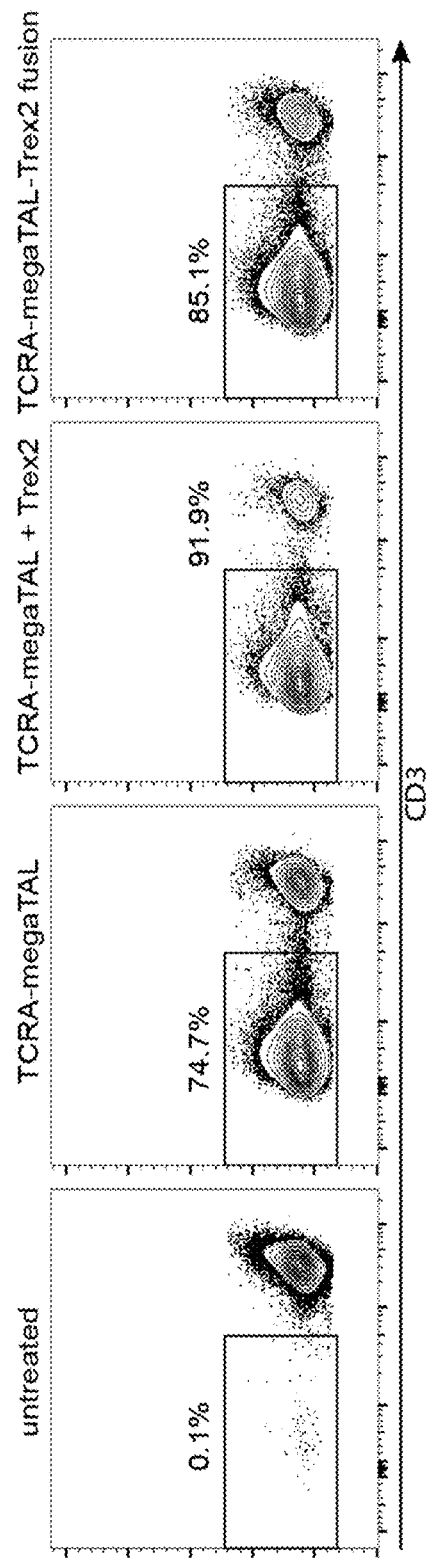
FIG. 15 shows efficient TCRA gene inactivation in primary human T cells via electroporation with an mRNA species encoding a three component TAL-LHE-Trex2 fusion protein.

A chimeric endonuclease architecture that could improve the efficiency of the TRAC-targeting LHE was created. As described herein, TALE proteins offer a uniquely modular mode of DNA recognition. The invertors therefore reasoned that an array of TALE repeats which recognized a target sequence adjacent to the TCRA_S02 target could be fused to the TCRA_S02 targeting LHE to effectively enhance the co-localization of the nuclease and its substrate. See FIG. 13 which schematically illustrates the chimeric endonuclease and its recognition sequence (SEQ ID NO: 3). This chimeric endonuclease (SEQ ID NO: 14 encoded by SEQ ID NO: 13)—an architecture termed 'MegaTAL'—was then converted into mRNA by in vitro transcription methods described above. IVT-mRNA species encoding the TCRA_S02 targeting MegaTAL and the Trex2 exonuclease were then delivered by electroporation to primary human T cells. This method of transiently expressing these nuclease reagents resulted in extremely efficient removal of the TCR-alpha protein from the cell surface. See FIG. 14 which demonstrates the effectiveness of this approach using flow cytometric analysis of TCR-alpha expression on primary T cells treated with IVT-mRNA species encoding the mega-TAL and Trex2 exonuclease, as >65% of cells lacked TCR-alpha expression.

Example 6: TCRA-Targeting, TALE-LHE Fusions were Improved by Fusion with Trex2, Enabling Ultra-Efficient TCRA Gene Disruption with a Three-Component Fusion Protein Expressed from a Single mRNA Species Next, efficient TCRA gene disruption was evaluated for achievement by delivering a single mRNA species expressing a fusion protein comprising a TAL array, the TCRA.S02 targeting LHE, and Trex2. This three-component fusion protein (SEQ ID NO: 16 encoded by SEQ ID NO: 15) was placed in a vector containing a T7 promoter to facilitate in vitro transcription and subsequent polyadenylation and capping. The resulting mRNA was delivered to primary human T cells by electroporation and the expression of the CD3 complex on the cell surface was assessed 72 hours later by flow cytometry (FIG. 16). Control samples included untransfected primary human T cells, T cells transfected with the TCRA.S02 targeting MegaTAL, and a sample where the TCRA.S02 targeting MegaTAL was cotransfected with an independently synthesized mRNA species encoding Trex2. The samples receiving Trex2 either independently or as a direct fusion with the TCRA.S02 targeting MegaTAL showed an increased percentage of CD3 negative cells, indicating enhanced TCRA gene disruption rates in these samples.

REFERENCES

Arimondo, P. B., C. J. Thomas, et al. (2006). "Exploring the cellular activity of camptothecin-triple-helix-forming oligonucleotide conjugates." *Mol Cell Biol* 26(1): 324-33.

Baxter, S., A. R. Lambert, et al. (2012). "Engineering domain fusion chimeras from I-Onul family LAGLIDADG homing endonucleases." *Nucleic Acids Res.*

Bitinaite, J., D. A. Wah, et al. (1998). "FokI dimerization is required for DNA cleavage." *Proc Natl Acad Sci USA* 95(18): 10570-5.

Boch, J., H. Scholze, et al. (2009). "Breaking the code of DNA binding specificity of TAL-type III effectors." *Science* 326(5959): 1509-12.

Choulika, A., A. Perrin, et al. (1995). "Induction of homologous recombination in mammalian chromosomes by using the I-SceI system of *Saccharomyces cerevisiae*." *Mol Cell Biol* 15(4): 1968-73.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Eisenschmidt, K., T. Lanio, et al. (2005). "Developing a programmed restriction endonuclease for highly specific DNA cleavage." *Nucleic Acids Res* 33(22): 7039-47.

Jarjour, J., H. West-Foyle, et al. (2009). "High-resolution profiling of homing endonuclease binding and catalytic specificity using yeast surface display." *Nucleic Acids Res* 37(20): 6871-80.

Jinek, M., K. Chylinski, et al. (2012). "A programmable dual-RNA-guided DNA endonuclease in adaptive bacterial immunity." *Science* 337(6096): 816-21.

Kalish, J. M. and P. M. Glazer (2005). "Targeted genome modification via triple helix formation." *Ann N Y Acad Sci* 1058: 151-61.

Kim, Y. G., J. Cha, et al. (1996). "Hybrid restriction enzymes: zinc finger fusions to Fok I cleavage domain." *Proc Natl Acad Sci USA* 93(3): 1156-60.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knock-out and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mali, P., L. Yang, et al. (2013). "RNA-guided human genome engineering via Cas9." *Science* 339(6121): 823-6.

Moore, I., M. Samalova, et al. (2006). "Transactivated and chemically inducible gene expression in plants." *Plant J* 45(4): 651-83.

Moscou, M. J. and A. J. Bogdanove (2009). "A simple cipher governs DNA recognition by TAL effectors." *Science* 326(5959): 1501.

Pabo, C. O., E. Peisach, et al. (2001). "Design and selection of novel Cys2His2 zinc finger proteins." *Annu Rev Biochem* 70: 313-40.

Padidam, M., M. Gore, et al. (2003). "Chemical-inducible, ecdysone receptor-based gene expression system for plants." *Transgenic Res* 12(1): 101-9.

Paques, F. and P. Duchateau (2007). "Meganucleases and DNA double-strand break-induced recombination: perspectives for gene therapy." *Curr Gene Ther* 7(1): 49-66.

Perrin, A., M. Buckle, et al. (1993). "Asymmetrical recognition and activity of the I-SceI endonuclease on its site and on intron-exon junctions." *Embo J* 12(7): 2939-47.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Rouet, P., F. Smih, et al. (1994). "Expression of a site-specific endonuclease stimulates homologous recombination in mammalian cells." *Proc Natl Acad Sci USA* 91(13): 6064-8.

Rouet, P., F. Smih, et al. (1994). "Introduction of double-strand breaks into the genome of mouse cells by expression of a rare-cutting endonuclease." *Mol Cell Biol* 14(12): 8096-106.

Sethuraman, J., A. Majer, et al. (2009). "Genes within genes: multiple LAGLIDADG homing endonucleases target the ribosomal protein S3 gene encoded within an rnl group I intron of *Ophiostoma* and related taxa." *Mol Biol Evol* 26(10): 2299-315.

Simon, P., F. Cannata, et al. (2008). "Sequence-specific DNA cleavage mediated by bipyridine polyamide conjugates." *Nucleic Acids Res* 36(11): 3531-8.

Smith, J., J. M. Berg, et al. (1999). "A detailed study of the substrate specificity of a chimeric restriction enzyme." *Nucleic Acids Res* 27(2): 674-81.

Smith, J., M. Bibikova, et al. (2000). "Requirements for double-strand cleavage by chimeric restriction enzymes with zinc finger DNA-recognition domains." *Nucleic Acids Res* 28(17): 3361-9.

Takeuchi, R., A. R. Lambert, et al. (2011). "Tapping natural reservoirs of homing endonucleases for targeted gene modification." *Proc Natl Acad Sci USA* 108(32): 13077-82.

Thierry, A. and B. Dujon (1992). "Nested chromosomal fragmentation in yeast using the meganuclease I-Sce I: a new method for physical mapping of eukaryotic genomes." *Nucleic Acids Res* 20(21): 5625-31.

Wang, R., X. Zhou, et al. (2003). "Chemically regulated expression systems and their applications in transgenic plants." *Transgenic Res* 12(5): 529-40.

Zuo, J. and N. H. Chua (2000). "Chemical-inducible systems for regulated expression of plant genes." *Curr Opin Biotechnol* 11(2): 146-51.

The invention claimed is:

1. A polypeptide comprising an I-OnuI variant having at least 70% sequence identity with the amino acid sequence of SEQ ID NO: 6, SEQ ID NO: 8, or SEQ ID NO: 10,
   wherein said I-OnuI variant cleaves a target nucleic acid sequence within the T cell receptor alpha constant gene (TRAC),
   wherein said I-OnuI variant is fused to a TALE DNA binding domain.

2. The polypeptide of claim 1 comprising an I-OnuI variant having at least 10 amino acid substitutions in positions selected from the group consisting of: 19, 24, 26, 28, 30, 32, 34, 35, 36, 37, 38, 40, 42, 44, 46, 48, 68, 70, 72, 75, 76, 77, 78, 80, 82, 138, 159, 168, 178, 180, 182, 184, 186, 188, 189, 190, 191, 192, 193, 195, 197, 199, 201, 203, 207, 223, 225, 227, 229, 231, 232, 234, 236, 238, 240, in reference to SEQ ID NO: 2.

3. The polypeptide of claim 1 comprising an I-OnuI variant having at least 15 amino acid substitutions in positions selected from the group consisting of: 19, 24, 26, 28, 30, 32, 34, 35, 36, 37, 38, 40, 42, 44, 46, 48, 68, 70, 72, 75, 76, 77, 78, 80, 82, 138, 159, 168, 178, 180, 182, 184, 186, 188, 189, 190, 191, 192, 193, 195, 197, 199, 201, 203, 207, 223, 225, 227, 229, 231, 232, 234, 236, 238, 240, in reference to SEQ ID NO: 2.

4. The polypeptide of claim 1 comprising an I-OnuI variant having at least 20 amino acid substitutions in positions selected from the group consisting of: 19, 24, 26, 28, 30, 32, 34, 35, 36, 37, 38, 40, 42, 44, 46, 48, 68, 70, 72, 75, 76, 77, 78, 80, 82, 138, 159, 168, 178, 180, 182, 184, 186, 188, 189, 190, 191, 192, 193, 195, 197, 199, 201, 203, 207, 223, 225, 227, 229, 231, 232, 234, 236, 238, 240, in reference to SEQ ID NO: 2.

5. The polypeptide of claim 1 comprising an I-OnuI variant having at least 25 amino acid substitutions in positions selected from the group consisting of positions: 19, 24, 26, 28, 30, 32, 34, 35, 36, 37, 38, 40, 42, 44, 46, 48, 68, 70, 72, 75, 76, 77, 78, 80, 82, 138, 159, 168, 178, 180, 182, 184, 186, 188, 189, 190, 191, 192, 193, 195, 197, 199, 201, 203, 207, 223, 225, 227, 229, 231, 232, 234, 236, 238, and 240, in reference to SEQ ID NO: 2.

6. The polypeptide of claim 1 comprising an I-OnuI variant having at least 75% sequence identity with the amino acid sequence of SEQ ID NO: 6, SEQ ID NO: 8, or SEQ ID NO: 10.

7. The polypeptide of claim 1 comprising an I-OnuI variant having at least 80% sequence identity with the amino acid sequence of SEQ ID NO: 6, SEQ ID NO: 8, or SEQ ID NO: 10.

8. The polypeptide of claim 1 comprising an I-OnuI variant having at least 85% sequence identity with the amino acid sequence of SEQ ID NO: 6, SEQ ID NO: 8, or SEQ ID NO: 10.

9. The polypeptide of claim 1 comprising an I-OnuI variant having at least 90% sequence identity with the amino acid sequence of SEQ ID NO: 6, SEQ ID NO: 8, or SEQ ID NO: 10.

10. The polypeptide of claim 1 comprising an I-OnuI variant having at least 95% sequence identity with the amino acid sequence of SEQ ID NO: 6, SEQ ID NO: 8, or SEQ ID NO: 10.

11. The polypeptide of claim 1 comprising an I-OnuI variant comprising the amino acid sequence of SEQ ID NO: 6.

12. The polypeptide of claim 1 comprising an I-OnuI variant comprising the amino acid sequence of SEQ ID NO: 8.

13. The polypeptide of claim 1 comprising an I-OnuI variant comprising the amino acid sequence of SEQ ID NO: 10.

14. The polypeptide of claim 1, comprising the MegaTAL TCRA_S02 amino acid sequence of SEQ ID NO: 14.

15. The polypeptide of claim 1, comprising the MegaTAL TCRA_S02 amino acid sequence of SEQ ID NO: 16.

16. The polypeptide of claim 1, further comprising an additional protein domain that has catalytic activity selected from the group consisting of: nuclease activity, polymerase activity, kinase activity, phosphatase activity, methylase activity, topoisomerase activity, integrase activity, transposase activity, ligase activity, helicase activity, and recombinase activity.

17. The polypeptide of claim 16, wherein said catalytic domain is a 5'-3' exonuclease.

18. The polypeptide of claim 17, wherein said catalytic domain is Trex2.

19. The polypeptide of claim 17, wherein said catalytic domain is a single chain Trex2.

20. The polypeptide of claim 16, wherein said additional protein domain is fused to the polypeptide by a peptide linker.

21. The polypeptide of claim 1, wherein it cleaves a target nucleic acid sequence of SEQ ID NO: 3.

* * * * *